(12) United States Patent
Krafft et al.

(10) Patent No.: US 8,536,381 B2
(45) Date of Patent: Sep. 17, 2013

(54) PROCESS FOR PURIFYING HYDROGEN CHLORIDE

(75) Inventors: Philippe Krafft, Rhode Saint Genese (BE); Patrick Gilbeau, Beaine-le-Comte (BE)

(73) Assignee: Solvay SA, Brussels (BE)

( * ) Notice: Subject to any disclaimer, the term of this patent is extended or adjusted under 35 U.S.C. 154(b) by 231 days.

(21) Appl. No.: 13/063,230

(22) PCT Filed: Sep. 11, 2009

(86) PCT No.: PCT/EP2009/061812
§ 371 (c)(1),
(2), (4) Date: Mar. 10, 2011

(87) PCT Pub. No.: WO2010/029153
PCT Pub. Date: Mar. 18, 2010

(65) Prior Publication Data
US 2011/0166369 A1    Jul. 7, 2011

(30) Foreign Application Priority Data

Sep. 12, 2008 (FR) ...................... 08 56138

(51) Int. Cl.
C07C 31/36    (2006.01)
C07C 29/62    (2006.01)

(52) U.S. Cl.
USPC .......................................... 568/844; 568/841

(58) Field of Classification Search
USPC ................................. 568/841, 844
See application file for complete search history.

(56) References Cited

U.S. PATENT DOCUMENTS

| | | |
|---|---|---|
| 280,893 A | 7/1883 | Baijjard |
| 865,727 A | 9/1907 | Queneau |
| 2,060,715 A | 11/1936 | Arvin |
| 2,063,891 A | 12/1936 | Dreyfus |
| 2,144,612 A | 1/1939 | Britton et al. |
| 2,198,600 A | 4/1940 | Britton et al. |
| 2,248,635 A | 7/1941 | Marple et al. |
| 2,319,876 A | 5/1943 | Moss |
| 2,444,333 A | 6/1948 | Castan |
| 2,505,735 A | 4/1950 | Halbedel |
| 2,726,072 A | 12/1955 | Herman |
| 2,733,195 A | 1/1956 | Miller |
| 2,811,227 A | 10/1957 | O'Connor |
| 2,829,124 A | 4/1958 | Napravnik et al. |
| 2,860,146 A | 11/1958 | Furman et al. |
| 2,876,217 A | 3/1959 | Paschall |
| 2,945,004 A | 7/1960 | Greenlee |
| 2,960,447 A | 11/1960 | Anderson et al. |
| 3,026,270 A | 3/1962 | Robinson, Jr. |
| 3,052,612 A | 9/1962 | Henegar et al. |
| 3,061,615 A | 10/1962 | Viriot et al. |
| 3,121,727 A | 2/1964 | Baliker et al. |
| 3,135,705 A | 6/1964 | Vandenberg |
| 3,158,580 A | 11/1964 | Vandenberg |
| 3,158,581 A | 11/1964 | Vandenberg |
| 3,247,227 A | 4/1966 | White |
| 3,260,059 A | 7/1966 | Rosenberg et al. |
| 3,341,491 A | 9/1967 | Robinson et al. |
| 3,355,511 A | 11/1967 | Schwarzer |
| 3,385,908 A | 5/1968 | Schwarzer |
| 3,445,197 A | 5/1969 | Resh et al. |
| 3,457,282 A | 7/1969 | Polak et al. |
| 3,618,295 A | 11/1971 | Geiger et al. |
| 3,711,388 A | 1/1973 | Gritzner |
| 3,766,221 A | 10/1973 | Becker |
| 3,839,169 A | 10/1974 | Moyer |
| 3,865,886 A | 2/1975 | Schindler et al. |
| 3,867,166 A | 2/1975 | Sullivan |
| 3,879,180 A | 4/1975 | Hutgens et al. |
| 3,954,581 A | 5/1976 | Carlin |
| 3,968,178 A | 7/1976 | Obrecht et al. |
| 4,003,723 A | 1/1977 | Schafer et al. |
| 4,011,251 A | 3/1977 | Tjurin et al. |
| 4,024,301 A | 5/1977 | Witenhafer et al. |
| 4,104,434 A | 8/1978 | Johnson |
| 4,127,594 A | 11/1978 | Anderson et al. |
| 4,173,710 A | 11/1979 | Boulet et al. |
| 4,197,399 A | 4/1980 | Noel et al. |
| 4,220,529 A | 9/1980 | Daude-Lagrave |
| 4,240,885 A | 12/1980 | Suciu et al. |
| 4,255,470 A | 3/1981 | Cohen et al. |
| 4,294,776 A | 10/1981 | Hardy et al. |
| 4,309,394 A | 1/1982 | Hudson |
| 4,322,367 A | 3/1982 | Silvis |
| 4,390,680 A | 6/1983 | Nelson |
| 4,405,465 A | 9/1983 | Moore et al. |

(Continued)

FOREIGN PATENT DOCUMENTS

| | | |
|---|---|---|
| BE | 422877 A | 8/1937 |
| CN | 1135533 A | 11/1996 |

(Continued)

OTHER PUBLICATIONS

Ma Zengxin et al, "recovery of Polyglycerol from residues of Synthetic Glycerol" Riyong Huaxue Gongye, 1997, 4, 21023 (English Abstract only).

(Continued)

Primary Examiner — Elvis O Price
(74) Attorney, Agent, or Firm — Oblon, Spivak, McClelland, Maier & Neustadt, L.L.P.

(57) ABSTRACT

Process for purifying hydrogen chloride, comprising at least one step of bringing said hydrogen chloride into contact with a scrubbing agent containing at least one chlorohydrin.

15 Claims, 1 Drawing Sheet

(56) References Cited

U.S. PATENT DOCUMENTS

| | | |
|---|---|---|
| 4,415,460 A | 11/1983 | Suciu et al. |
| 4,464,517 A | 8/1984 | Makino et al. |
| 4,499,255 A | 2/1985 | Wang et al. |
| 4,560,812 A | 12/1985 | Blytas |
| 4,595,469 A | 6/1986 | Foller |
| 4,599,178 A | 7/1986 | Blytas |
| 4,609,751 A | 9/1986 | Hajjar |
| 4,634,784 A | 1/1987 | Nagato et al. |
| 4,655,879 A | 4/1987 | Brockmann et al. |
| 4,898,644 A | 2/1990 | Van Horn |
| 4,935,220 A | 6/1990 | Schneider et al. |
| 4,960,953 A | 10/1990 | Jakobson et al. |
| 4,973,763 A | 11/1990 | Jakobson et al. |
| 4,990,695 A | 2/1991 | Buenemann et al. |
| 5,041,688 A | 8/1991 | Jakobson et al. |
| 5,200,163 A | 4/1993 | Henkelmann et al. |
| 5,278,260 A | 1/1994 | Schaffner et al. |
| 5,286,354 A | 2/1994 | Bard et al. |
| 5,344,945 A | 9/1994 | Grunchard |
| 5,359,094 A | 10/1994 | Teles et al. |
| 5,393,428 A | 2/1995 | Dilla et al. |
| 5,445,741 A | 8/1995 | Dilla et al. |
| 5,478,472 A | 12/1995 | Dilla et al. |
| 5,486,627 A | 1/1996 | Quarderer et al. |
| 5,567,359 A | 10/1996 | Cassidy et al. |
| 5,578,740 A | 11/1996 | Au et al. |
| 5,679,839 A | 10/1997 | Armand et al. |
| 5,710,350 A | 1/1998 | Jeromin et al. |
| 5,731,476 A | 3/1998 | Shawl et al. |
| 5,744,655 A | 4/1998 | Thomas et al. |
| 5,766,270 A | 6/1998 | Neuman et al. |
| 5,779,915 A | 7/1998 | Becker et al. |
| 5,908,946 A | 6/1999 | Stern et al. |
| 5,955,043 A | 9/1999 | Neuman et al. |
| 5,993,974 A | 11/1999 | Fukushima et al. |
| 6,024,839 A | 2/2000 | Schufeldt |
| 6,103,092 A | 8/2000 | Silva |
| 6,111,153 A | 8/2000 | Crow et al. |
| 6,142,458 A | 11/2000 | Howk |
| 6,177,599 B1 | 1/2001 | Cowfer et al. |
| 6,270,682 B1 | 8/2001 | Santen et al. |
| 6,288,248 B1 | 9/2001 | Strebelle et al. |
| 6,288,287 B2 | 9/2001 | Ueoka et al. |
| 6,350,888 B1 | 2/2002 | Strebelle et al. |
| 6,350,922 B1 | 2/2002 | Vosejpka et al. |
| 6,428,759 B1 | 8/2002 | Smith et al. |
| 6,521,794 B2 | 2/2003 | Hirota |
| 6,589,497 B2 | 7/2003 | Smith |
| 6,719,957 B2 | 4/2004 | Brady, Jr. et al. |
| 6,740,633 B2 | 5/2004 | Norenberg et al. |
| 6,806,396 B2 | 10/2004 | Gelblum et al. |
| 6,831,201 B2 | 12/2004 | Katsuura et al. |
| 7,126,032 B1 | 10/2006 | Aiken |
| 7,128,890 B2 | 10/2006 | Ollivier |
| 7,453,008 B2 | 11/2008 | Ko et al. |
| 7,557,253 B2 | 7/2009 | Gilbeau |
| 7,584,629 B2 | 9/2009 | Sohn et al. |
| 7,615,670 B2 | 11/2009 | Gilbeau |
| 7,619,056 B2 | 11/2009 | East et al. |
| 8,106,246 B2 | 1/2012 | Krafft et al. |
| 2001/0014763 A1 | 8/2001 | Ueoka et al. |
| 2003/0209490 A1 | 11/2003 | Camp et al. |
| 2004/0016411 A1 | 1/2004 | Joyce et al. |
| 2004/0024244 A1 | 2/2004 | Walsdorff et al. |
| 2004/0047781 A1 | 3/2004 | Becenel, Jr. |
| 2004/0150123 A1 | 8/2004 | Strofer et al. |
| 2004/0179987 A1 | 9/2004 | Oku et al. |
| 2004/0232007 A1 | 11/2004 | Carson et al. |
| 2005/0115901 A1 | 6/2005 | Heuser et al. |
| 2005/0261509 A1 | 11/2005 | Delfort et al. |
| 2006/0052272 A1 | 3/2006 | Meli et al. |
| 2006/0079433 A1 | 4/2006 | Hecht et al. |
| 2006/0123842 A1 | 6/2006 | Sohn et al. |
| 2007/0112224 A1 | 5/2007 | Krafft et al. |
| 2007/0251831 A1 | 11/2007 | Kaczur et al. |
| 2007/0293707 A1 | 12/2007 | Wolfert et al. |
| 2008/0021209 A1 | 1/2008 | East et al. |
| 2008/0053836 A1 | 3/2008 | Bulan et al. |
| 2008/0146753 A1 | 6/2008 | Woike et al. |
| 2008/0154050 A1 | 6/2008 | Gilbeau |
| 2008/0161613 A1 | 7/2008 | Krafft et al. |
| 2008/0194847 A1 | 8/2008 | Krafft et al. |
| 2008/0194849 A1 | 8/2008 | Krafft et al. |
| 2008/0194850 A1 | 8/2008 | Krafft et al. |
| 2008/0194851 A1 | 8/2008 | Gilbeau |
| 2008/0200642 A1 | 8/2008 | Krafft |
| 2008/0200701 A1 | 8/2008 | Krafft et al. |
| 2008/0207930 A1 | 8/2008 | Gilbeau et al. |
| 2008/0214848 A1 | 9/2008 | Krafft et al. |
| 2008/0281132 A1 | 11/2008 | Krafft et al. |
| 2009/0022653 A1 | 1/2009 | Strebelle et al. |
| 2009/0131631 A1 | 5/2009 | Krafft et al. |
| 2009/0173636 A1 | 7/2009 | Ooms et al. |
| 2009/0198041 A1 | 8/2009 | Krafft et al. |
| 2009/0270588 A1 | 10/2009 | Krafft et al. |
| 2009/0275726 A1 | 11/2009 | Krafft et al. |
| 2010/0029959 A1 | 2/2010 | Fan et al. |
| 2010/0032617 A1 | 2/2010 | Gilbeau et al. |
| 2010/0105862 A1 | 4/2010 | Krafft et al. |
| 2010/0105964 A1 | 4/2010 | Krafft et al. |
| 2010/0168379 A1 | 7/2010 | Krafft et al. |
| 2010/0170805 A1 | 7/2010 | Krafft et al. |
| 2010/0179300 A1 | 7/2010 | Boulos et al. |
| 2010/0179302 A1 | 7/2010 | Krafft et al. |
| 2010/0212540 A1 | 8/2010 | Bobet et al. |
| 2010/0294727 A1 | 11/2010 | Gilbeau et al. |
| 2010/0305271 A1 | 12/2010 | Mentink et al. |
| 2010/0305367 A1 | 12/2010 | Borremans |
| 2010/0311874 A1 | 12/2010 | Mentink et al. |
| 2010/0311905 A1 | 12/2010 | Mentink et al. |
| 2010/0311942 A1 | 12/2010 | Gilbeau et al. |
| 2011/0028683 A1 | 2/2011 | Gilbeau et al. |
| 2011/0086949 A1 | 4/2011 | Mentink et al. |
| 2011/0118390 A1 | 5/2011 | Feron et al. |
| 2011/0152545 A1 | 6/2011 | Balthasart et al. |
| 2011/0166369 A1 | 7/2011 | Krafft et al. |
| 2011/0195148 A1 | 8/2011 | Mentink et al. |
| 2011/0237773 A1 | 9/2011 | Gilbeau |
| 2012/0010420 A1 | 1/2012 | Gilbeau et al. |
| 2012/0199493 A1 | 8/2012 | Krafft et al. |
| 2012/0199786 A1 | 8/2012 | Gilbeau |
| 2013/0032755 A1 | 2/2013 | Gilbeau |

FOREIGN PATENT DOCUMENTS

| | | |
|---|---|---|
| CN | 1296003 A | 5/2001 |
| CN | 101041421 | 9/2007 |
| DE | 58396 C | 8/1891 |
| DE | 180668 C | 1/1906 |
| DE | 197308 C | 11/1906 |
| DE | 238341 C | 3/1908 |
| DE | 197309 C | 4/1908 |
| DE | 869193 | 3/1953 |
| DE | 1041488 B | 10/1958 |
| DE | 1075103 B | 2/1960 |
| DE | 1226554 B | 10/1966 |
| DE | 2 241 393 | 2/1974 |
| DE | 25 21 813 | 12/1975 |
| DE | 3003819 A1 | 8/1981 |
| DE | 3243617 | 5/1984 |
| DE | 216471 A1 | 12/1984 |
| DE | 3721003 C1 | 12/1988 |
| DE | 4302306 | 8/1994 |
| DE | 4335311 A1 | 4/1995 |
| DE | 10203914 C1 | 10/2003 |
| DE | 10254709 A1 | 6/2004 |
| EP | 0563720 A1 | 10/1893 |
| EP | 0 296 341 | 12/1988 |
| EP | 0 317 184 | 5/1989 |
| EP | 0 317 185 | 5/1989 |
| EP | 0317184 A2 | 5/1989 |
| EP | 0317185 A2 | 5/1989 |
| EP | 0347618 A2 | 12/1989 |
| EP | 0358255 A1 | 3/1990 |
| EP | 0421379 A1 | 4/1991 |

| | | | | | | |
|---|---|---|---|---|---|---|
| EP | 0 452 265 | 10/1991 | | JP | 5629572 | 3/1981 |
| EP | 0518765 A1 | 12/1992 | | JP | 5699432 | 8/1981 |
| EP | 0522382 A1 | 1/1993 | | JP | 56-155009 A | 12/1981 |
| EP | 0535949 B1 | 4/1993 | | JP | 60-258171 A | 12/1985 |
| EP | 0561441 A1 | 9/1993 | | JP | 61-044833 A | 3/1986 |
| EP | 0568389 A1 | 11/1993 | | JP | 61 112066 A | 5/1986 |
| EP | 0582201 A2 | 2/1994 | | JP | 61-140532 A | 6/1986 |
| EP | 0618170 | 10/1994 | | JP | 61236749 A | 10/1986 |
| EP | 0 916 624 | 5/1999 | | JP | 62242638 A | 10/1987 |
| EP | 0919551 A1 | 6/1999 | | JP | 63195288 A | 8/1988 |
| EP | 0774450 | 2/2000 | | JP | 2-137704 | 5/1990 |
| EP | 0979671 A1 | 2/2000 | | JP | 03014527 A | 1/1991 |
| EP | 1059278 A2 | 12/2000 | | JP | 3223267 A | 10/1991 |
| EP | 1106237 A1 | 6/2001 | | JP | 03223267 A | 10/1991 |
| EP | 1153887 A2 | 11/2001 | | JP | 04089440 A | 3/1992 |
| EP | 1163946 A1 | 12/2001 | | JP | 04-217637 | 8/1992 |
| EP | 1298154 A1 | 4/2003 | | JP | 6-9589 A | 1/1994 |
| EP | 1411027 A1 | 4/2004 | | JP | 625196 B2 | 4/1994 |
| EP | 1752435 A1 | 2/2007 | | JP | 06184024 A | 7/1994 |
| EP | 1752436 A1 | 2/2007 | | JP | 6321852 A | 11/1994 |
| EP | 1760060 A1 | 3/2007 | | JP | 08-003087 A | 1/1996 |
| EP | 1762556 A1 | 3/2007 | | JP | 859593 | 3/1996 |
| EP | 1770081 A1 | 4/2007 | | JP | 09-2999953 | 11/1997 |
| EP | 1772446 A1 | 4/2007 | | JP | 10139700 A | 5/1998 |
| EP | 1775278 A1 | 4/2007 | | JP | 10218810 A | 8/1998 |
| EP | 2085364 | 8/2009 | | JP | 1998218810 | 8/1998 |
| FR | 1056360 A | 2/1954 | | JP | 20000344692 A | 12/2000 |
| FR | 1 306 231 | 10/1961 | | JP | 2001-037469 | 2/2001 |
| FR | 1 417 388 | 10/1964 | | JP | 2001-213827 A | 8/2001 |
| FR | 1 577 792 | 8/1965 | | JP | 2001-261308 | 9/2001 |
| FR | 1476073 A | 4/1967 | | JP | 2001-1261581 A | 9/2001 |
| FR | 2151107 | 4/1973 | | JP | 2001276572 A | 10/2001 |
| FR | 2180138 | 5/1973 | | JP | 2002-02033 A2 | 1/2002 |
| FR | 2 217 372 | 2/1974 | | JP | 20020038195 A | 2/2002 |
| FR | 2565229 A1 | 12/1985 | | JP | 20020265986 A | 9/2002 |
| FR | 2752242 A1 | 2/1998 | | JP | 2002-363153 A | 12/2002 |
| FR | 2862644 A1 | 5/2005 | | JP | 2003-89680 A | 3/2003 |
| FR | 2868419 A1 | 10/2005 | | JP | 2003081891 A | 3/2003 |
| FR | 2869612 A1 | 11/2005 | | JP | 2003183191 A | 7/2003 |
| FR | 2869613 A1 | 11/2005 | | JP | 2003206473 A | 7/2003 |
| FR | 2872504 A1 | 1/2006 | | JP | 2004518102 A | 6/2004 |
| FR | 2881732 A1 | 8/2006 | | JP | 2004216246 A | 8/2004 |
| FR | 2885903 A1 | 11/2006 | | JP | 2005007841 A2 | 1/2005 |
| FR | 2 912 743 | 8/2008 | | JP | 2005097177 A | 4/2005 |
| FR | 2913683 | 9/2008 | | JP | 2005513064 A | 5/2005 |
| FR | 2913683 A1 | 9/2008 | | JP | 2005-154292 A | 6/2005 |
| FR | 2917411 | 12/2008 | | JP | 2009-263338 | 11/2009 |
| FR | 2918058 A1 | 1/2009 | | KR | 900006513 | 11/1987 |
| FR | 2925045 A1 | 6/2009 | | KR | 1019920003099 B1 | 4/1992 |
| FR | 2 927 083 | 8/2009 | | KR | 10-514819 B1 | 9/2005 |
| FR | 2927083 A1 | 8/2009 | | PL | 136598 | 3/1986 |
| FR | 2929611 A1 | 10/2009 | | PL | 162910 | 1/1994 |
| FR | 2935699 A1 | 3/2010 | | SU | 123153 | 1/1959 |
| GB | 14767 A | 1/1914 | | SU | 1125226 | 11/1984 |
| GB | 406345 | 8/1932 | | SU | 1159716 | 6/1985 |
| GB | 404938 A | 1/1934 | | SU | 1685969 | 10/1991 |
| GB | 467481 A | 6/1937 | | WO | WO 95/14635 A1 | 6/1995 |
| GB | 541357 A | 11/1941 | | WO | WO 95/14639 | 6/1995 |
| GB | 679536 A | 9/1952 | | WO | WO 96/15980 | 5/1996 |
| GB | 702143 A | 1/1954 | | WO | WO 97/48667 | 12/1997 |
| GB | 724222 A | 2/1955 | | WO | WO 96/07617 | 3/1998 |
| GB | 736641 A | 9/1955 | | WO | WO 98/37024 | 8/1998 |
| GB | 758665 A | 10/1956 | | WO | WO 99/14208 | 3/1999 |
| GB | 799567 A | 8/1958 | | WO | WO 9932397 A1 | 7/1999 |
| GB | 984446 A | 2/1965 | | WO | WO 0024674 A1 | 5/2000 |
| GB | 984633 A | 3/1965 | | WO | WO 01/43762 A2 | 6/2001 |
| GB | 1046521 A | 10/1966 | | WO | WO 0141919 A1 | 6/2001 |
| GB | 1083594 A | 9/1967 | | WO | WO 0186220 A2 | 11/2001 |
| GB | 1286893 A | 8/1972 | | WO | WO 02/26672 A2 | 4/2002 |
| GB | 1387668 A | 3/1975 | | WO | 1231189 A1 | 8/2002 |
| GB | 1 493 538 | 4/1975 | | WO | WO 02059536 A1 | 8/2002 |
| GB | 1414976 A | 11/1975 | | WO | WO 03/064357 | 8/2003 |
| GB | 2173496 A | 10/1986 | | WO | WO 2004/056758 | 7/2004 |
| GB | 2336584 A | 10/1999 | | WO | WO 2005021476 A1 | 3/2005 |
| HU | 2002-003023 | 3/2004 | | WO | WO 2005054167 A1 | 6/2005 |
| JP | 3927230 B2 | 11/1939 | | WO | WO 2005/075189 | 8/2005 |
| JP | 50-062909 | 5/1975 | | WO | WO 2005/075189 A2 | 8/2005 |
| JP | 51021635 B | 7/1976 | | WO | WO 2005/097722 | 10/2005 |
| JP | 55041858 A | 3/1980 | | WO | WO 2005/115954 | 12/2005 |

| | | |
|---|---|---|
| WO | WO 2005/116004 | 12/2005 |
| WO | WO 2006020234 A1 | 2/2006 |
| WO | WO 2006100311 A2 | 9/2006 |
| WO | WO 2006100312 A2 | 9/2006 |
| WO | WO 2006100313 A2 | 9/2006 |
| WO | WO 2006100314 A1 | 9/2006 |
| WO | WO 2006100315 A2 | 9/2006 |
| WO | WO 2006100316 A1 | 9/2006 |
| WO | WO 2006100317 A1 | 9/2006 |
| WO | WO 2006100318 A2 | 9/2006 |
| WO | WO 2006100319 A1 | 9/2006 |
| WO | WO 2006100320 A2 | 9/2006 |
| WO | WO 2006106153 A2 | 10/2006 |
| WO | WO 2006106154 A1 | 10/2006 |
| WO | WO 2006106155 A2 | 10/2006 |
| WO | 2007-008898 | 1/2007 |
| WO | WO 2007054505 A2 | 5/2007 |
| WO | WO2007/144335 | 12/2007 |
| WO | WO 2008/101866 | 8/2008 |
| WO | WO2008/107468 | 9/2008 |
| WO | WO 2008/110588 | 9/2008 |
| WO | WO2008/145729 | 12/2008 |
| WO | WO 2008/147473 | 12/2008 |
| WO | WO 2008/152043 | 12/2008 |
| WO | WO 2008/152044 | 12/2008 |
| WO | WO 2008/152045 | 12/2008 |
| WO | WO2009/000773 | 12/2008 |
| WO | WO 2008152043 A1 | 12/2008 |
| WO | WO 2009/016149 A2 | 2/2009 |
| WO | WO 2009026212 A1 | 2/2009 |
| WO | WO 2009/043796 A1 | 4/2009 |
| WO | WO 2009/077528 | 6/2009 |
| WO | WO 2009/077528 A1 | 6/2009 |
| WO | WO 2009/095429 A1 | 8/2009 |
| WO | WO 2009/095617 | 8/2009 |
| WO | WO 2009/095617 A2 | 8/2009 |
| WO | WO 2009/095618 | 8/2009 |
| WO | WO 2009/095618 A2 | 8/2009 |
| WO | WO 2009/095622 | 8/2009 |
| WO | WO 2009/095622 A2 | 8/2009 |
| WO | WO 2009/121853 | 10/2009 |
| WO | WO 2009/121853 A1 | 10/2009 |
| WO | WO 2009/150382 A2 | 12/2009 |
| WO | WO 2009/150385 | 12/2009 |
| WO | WO 2010/010282 | 1/2010 |
| WO | WO 2010/010282 A1 | 1/2010 |
| WO | WO 2010/029039 | 3/2010 |
| WO | WO 2010/029039 A1 | 3/2010 |
| WO | WO 2010/043813 | 4/2010 |
| WO | WO 2010/043813 A1 | 4/2010 |
| WO | WO 2010/066660 | 6/2010 |
| WO | WO 2010/136725 | 12/2010 |
| WO | WO 2010/136725 A1 | 12/2010 |
| WO | WO 2011054769 A2 | 5/2011 |
| WO | WO 2011054770 A1 | 5/2011 |
| WO | WO 2012025468 A1 | 1/2012 |
| WO | WO 2012016872 A1 | 2/2012 |
| WO | WO 2012/041816 | 4/2012 |
| WO | WO 2012/041816 A1 | 4/2012 |
| WO | WO 2012/056005 | 5/2012 |

OTHER PUBLICATIONS

Sang Hee Lee et al "Direct preparation of Dichloropropanol (DCP) from Glycerol Using Heteropolyacid (HPA) Catalysts: A Catalyst Screen Study," Catalysis Communications (9), 2008, p. 1920-1923.
Production and Prospect of the World Natural Glycercl by Zhu Shiyong, Cereals and Oils, vol. 1, 1997, pp. 33-38 (No English Translation).
Vinnolit; Vinnolit receives EU grant for water recycling project: Press Release, 2008: http://www.vinnolit.de/vinnolit.nsf/id/EN_Vinnolit_receives_EU_grant_for_water_recycling_project_.
N.W. Ziets, Journal of American Oil Chemists' Society, Nov. 1956, vol. 33, pp. 556-565.
Perry's Chemical Engineers Handbook, Sixth Edition, McGraw Hill Inc., (1984) Section 18.
Vol. 83: Unit Operastions II of Ullmans's Encyclopedia of Industrial Chemistry, Fifth Completely Revised Edition, Published by VCH, 1988.
W. Geiger et al, "14C/12C-Ratios in Organic Matter and Hydrocarbons Extracted from Dated Lake Sediments", Nuclear Instruments and Methods in Physics Research B5 (1984), pp. 394-397, XP-002631954.
Jurgen O. Metzger, "Fats and Oils as Renewable Feedstock for Chemistry," Eur. J. Lipid Sci. Technol. (2009), vol. 111, pp. 865-876, XP-002631953.
Bruce M. Bell, "Glycerin as a Renewable Feedstock for Epichlorohydrin Production. The GTE Process", Clean-Soil, Air, Water, (2008) vol. 36, No. 8, pp. 657-661, XP-002631952.
[Unknown Author]—New Experimental Chemical Course 1, Basic Operation I, Section 4, Separation and Purification, pp. 251-252 (issued on Sep. 20, 1975) with English translation from Shiga International Patent Office, 3 pgs.
March, Jerry—"Reactions, Mechanisms & Structure", Advanced Organic Chemistry, 4$^{th}$ Ed., 1992, pp. 889, 908 and 937; 5 pgs.
[Unknown Author]—Bulletin de la Société Chimique de Paris—"Analyse des Travaux de Chimie Pure et Appliquée", G. Masson, Editor, Paris, Jul. 4, 1873, Novelle Série, Tome XIX, pp. 97-99; 4 pgs ; comments regarding Friedel & Silva's work on middle of p. 98.
Neuberg, Irene Stephanie—"A New Way of Preparing Glyceraldehyde from Glycerol", Kaiser Wilhelm Institute in Berlin for Biochemi-Dahlem, 1930; 3 pgs; Includes abstract in English.
Krausz, Francois—'Recherches sur les Aldehydes Substitues en α en β. α and β Substituted Aldehydes', University Strasbourg, France ; Ann Chim 12, Nov.-Dec. 1949, 4, pp. 811-831, 23 pgs ; Includes abstract in English.
[Unknown Author]—"Glycerine-An Overview"—by The Soap and Detergent Association, Glycerine and Oleochemical Division, 1990; 27 pgs.
[Unknown Author]—"Commercial Synthesis of Glycerol Begins a New Shell Chemical Corp Plant—A staff Report"; Chemical & Engineering News, 1948, vol. 26, No. 38, pp. 2770-2771; 2 pgs.
Fairbourne, Arthur, et al—"The Partial Esterification of Polyhydric Alcohols . Part XII . The Funstion of Ethylene-oxide Rings", J. Chem. Soc. 1932, republished 1965, , pp. 1965-1972; 8 pgs.
Clarke, H.T., et al—"Epichlorohydrin", Organic Syntheses, Coll. vol. 1, pp. 233 (1941) ; vol. 3, p. 47 (1923); 2 pgs.
Braun, Geza—"Epichlorohydrin and Epibromohydrin", Organic Syntheses, Coll. vol. 2, p. 256 (1943) ; vol. 16, p. 30 (1936); 2 pgs.
Conant, J.B., et al—"Glycerol a,y-Dichlorohydrin", Organic Syntheses, Coll. vol. 1, p. 292 (1941); vol. 2, p. 29 (1922); 3 pgs.
Chavanne, G.—"Memoires Presentes a La Societe Chimique", English translation—"Reports Submitted to Chemical Firm", Bull. Soc. Chim. Fr. 1943, 1, EP 06 121 086; 16 pgs.
Schroder, Angela, et al—"Glycerol as a by-product of biodiesel production in Diets for ruminants", 1999, The Regional Institute, Institute of Animal Nutrition, Physiology and Metabolism, University of Kiel, Germany, 6 pgs.
[Unknown Author]—"Chemical Properties and Derivatives of Glycerol", 1965, Glycerine Producer's Association, 1$^{st}$ Edition, 23 pgs.
Busby, G.W., et al—"The Purification of Glycerin by Ion-Exchange", The Journal of the American Oil Chemists' Society, 1952, 3 pgs.
Lamborn, Leebert Lloyd—"Modern Soaps, Candles and Glycerin", 3$^{rd}$ Edition, 1918, D. Van Nostrand Company, London, 12 pgs.
Knothe, Gerhard—"Historical perspectives on vegetable oil-based diesel fuels", Industrial Oils, 2001, vol. 12, pp. 1103-1107; 5 pgs.
Schuchardt, Ulf, et al—"Transesterification of Vegetable Oils: A Review", 1998, Braz. Chem Soc., vol. 9, No. 1, pp. 199-210; 12 pgs.
Claude, Sylvain—"Research of new outlets of glycerol-recent developments in France"—1999, Fett/Lipid, No. 3, Wiley-VCH Verlag GmbH, Weinheim, pp. 101-104; 4 pgs.
Prakash, Chandra B.—"A Critical Review of Biodiesel as a Transportation Fuel in Canada", 1998, GCSI-Global Change Strategies International Inc.; 119 pgs.
Fukuda, Hideki, et al—"Review—Biodiesel Fuel Production by Transesterification of Oils", 2001, Journal of Bioscience and Bioengineering; vol. 92, No. 5, pp. 405-416; 12 pgs.
Yong, K.C., et al—"Refining of Crude Glycerine Recovered From Glycerol Residue by Simple Vacuum Distillation", Dec. 2001, Journal of Oil Palm Research, vol. 13, No. 2, pp. 39-44, 6 pgs.

Wu, Guoying, et al—"Preparation of Biodiesel and Glycerol by Methyl Esterification of Cottonseed Oil", 2003, China Oil and Fat, vol. 28, Issue No. 4, pp. 70-73; 15 pgs; in Chinese; Translation provided in English.

Zhu, Shiyong—"Production and prospects of the world's natural glycerin", 1997, Cereals and Oils, Issue No. 01, pp. 33-38; 21pgs; in Chinese; Translation provided in English.

Hill, Arthur J., et al—"A Synthesis of Beta-Chloro-Allyl Chloride", 1922, Journal American Chemical Society, vol. 44, Issue No. 11, pp. 2582-2595; 15 pgs.

Physical and Chemical Dictionary (5th Edition), "Glass Lining"; "Porcelain Enamel", 1998; pp. 267, 378, 738, 1298 and 1403; 8 pgs; in Japanese; Partial translations provided in English for pp. 267 and 1298.

Encyclopedia Chimica, No. 8, (1st Edition), "Enamel, porcelain enamel, vitreous enamel"; 1962; 4 pgs; in Japanese; Partial translation provided in English.

Encyclopedia Chimica, No. 2, (1st Edition), "Glass lining", 1960; 4 pgs; in Japanese; Partial translation provided in English.

Gottlieb, Klaus, et al—"Glycerine—a sustainable raw material", 1994, Chem. Ing. Tech., vol. 66, Issue No. 1, pp. 64-66; 8 pgs; in German; Translation provided in English.

Wessendorf, Richard—"Glycerinderivate als Kraftstoffkomponenten", 1995, Wissenschaft & Technik, Science and Technology, pp. 138-143; 6 pgs; in German; no English translation provided.

Milchert, E., et al—"Dehydrochlorination of Glycerol Dichlorohydrin to Epichlorohydrin", 1995, Chem. Papers, vol. 49, Issue No. 3, pp. 133-136; 4 pgs.

Kaszonyi, A., et al—"Bioglycerol a new platform chemical", 2009, 44th International Petroleum Conference, Bratislava, Slovak Republic; pp. 1-8; 8 pgs.

Williamson, R., et al—"DE-FC36-03GO13000 Final Report: Continuous Isosorbide Production from Sorbitol using Solid Acid Catalysis", 2006, DOE Award for Iowa Corn Promotion Board; 9 pgs.

Malhotra, S. V., et al—"Applications of Corn-Based Chemistry", 2007, The Bridge Publication of the National Academy of Engineering, 2007, vol. 34, Issue No. 4; 8 pgs; Best copy available.

Jaffe, M., et al—"Corn (Sugars) Based Chemistries for the Polymer Industry", 2009, ANTEC, 67th Annual Technical Conf., Proceed., Society of Plastic Engineers, Jun. 22-24, Mc Cormick Place West Chigaco, IL, 6 pgs.

[Unknown Author]—"Iowa Corn Promotion Board, NJIT to License Breakthrough, Safe Bio-Plastic Alternative", Aug. 6, 2008, New Jersey Science & Technology University Press Release; 2 pgs.

[Unknown Author]—"NJIT Patent May Be Able to Replace BPA; Make Consumer Products Safer", Feb. 4, 2010, New Jersey Science & Technology University Press Release; 2 pgs.

Fenouillot, F., et al—"Polymers from renewable 1,4:3,6-dianhydrohexitols (isosorbide isomannide and isoidide): A Review", 2010, Progress in Polymer Science, vol. 35, Issue No. 5, pp. 578-622; 45 pgs.

U.S. Appl. No. 60/734,659, filed Nov. 8, 2005.
U.S. Appl. No. 60/734,627, filed Nov. 8, 2005.
U.S. Appl. No. 60/734,657, filed Nov. 8, 2005.
U.S. Appl. No. 60/734,658, filed Nov. 8, 2005.
U.S. Appl. No. 60/734,635, filed Nov. 8, 2005.
U.S. Appl. No. 60/734,634, filed Nov. 8, 2005.
U.S. Appl. No. 60/734,637, filed Nov. 8, 2005.
U.S. Appl. No. 60/734,636, filed Nov. 8, 2005.
U.S. Appl. No. 60/560,676, filed Apr. 8, 2004, Gilbeau, et al.
U.S. Appl. No. 61/013,680, filed Dec. 14, 2007, Krafft, et al.
U.S. Appl. No. 61/013,704, filed Dec. 14, 2007, Gilbeau, et al.
U.S. Appl. No. 61/013,713, filed Dec. 14, 2007, Gilbeau.
U.S. Appl. No. 61/013,676, filed Dec. 14, 2007, Borremans.
U.S. Appl. No. 61/013,707, filed Dec. 14, 2007, Krafft, et al.
U.S. Appl. No. 61/013,672, filed Dec. 14, 2007, Krafft, et al.
U.S. Appl. No. 61/013,710, filed Dec. 14, 2007, Krafft, et al.
U.S. Appl. No. 61/007,661, filed Dec. 14, 2007, Boulos, et al.

J.B. Conant, et al, "Glycerol a,y-dichlorohydrin", Organic Syntheses Coll., 1941, vol. 1, p. 292-294 (5 pp.).

Gilman H., Organic Synthesis, Section 1, pp. 234-235 (no date)—attached English translation only.

Industrial Chemical Encyclopedia 5, p. 457 (no date)—attached English translation only.

"Epoxy resins", p. 36-46, by Shangai Resin Plant, Shangai People's Press, 1971—attached English translation only.

Martinetti, R. et al. "Environnement Le Recyclage de l'eau" Industrie Textile, Ste Sippe Sarl, Metz, FR, No. 1300 (Jul. 1, 1998), ISSN: 0019-9176 (no English abstract available)—8 pp.

"Rainwater Harvesting and Utilization" (United Nations Environment Program) Mar. 2002; XP003003726; Internet Citation extracted online on Jan. 1, 2006: URL:http://www.unep.Or.ip/letc/Publication—4 pp.

Myszkowski, J. et al. "Removal of chlorinated organic impurities from hydrogen chloride"; English Chemical Abstract summary only of Polish Patent No. 136598 B2 (Mar. 13, 1986); XP002352444; 1 pp.

Myszkowski, J. et al. "Removal of organic compounds from gaseous hydrogen chloride by an absorption method" Chemia Stosowana (1986) vol. 30(4) p. 545-51; English Chemical Abstract Summary only; XP002352445; 1 pp.

Milchert, E. et al. "Recovering hydrogen chloride and organic chloro compounds from the reaction mixture in the chlorination of ethylene"; English Chemical Abstract Summary only of Polish Patent No. 162910 B1 (Jan. 31, 1994); XP002352443; 1 pp.

Laine, D.F. et al. "The destruction of organic pollutants under mild reaction conditions; A review" Michochemical Journal, vol. 85, No. 2, 2007 pp. 183-193; available online Aug. 17, 2006; 12 pp.

Clarke, H.T., et al—"Epichlorohydrin", "Ethyl Acetoacetate", 1964, Organic Syntheses, Collective vol. I, Being a Revised Edition of Annual vols. I-IX, Second Edition, Tenth Printing, John Wiley & Sons, Inc.; pp. 232-235; 6 pgs.

Braun, Geza—"Epichlorohydrin and Epibromohydrin", 1957, Organic Syntheses, Inc., Collective vol. 2, A Revised Edition of Annual vols. X-XIX, Eighth printing, John Wiley & Sons, Inc., pp. 256-258; 5 pgs.

Kirk-Othmer, Encyclopedia of Chemical Technology, Third Edition, vol. 9, Herman F. Mark, et al, Editors—"Epoxy Resins", 1980, pp. 267-290, A Wiley-Interscience Publication, John Wiley & Sons, Inc.; 28 pgs.

Encyclopedia of Experimental Chemistry I, Basic Operation I, edited by the Chemical Society of Japan Nov. 5, 1990, 4th Edition, pp. 161-165 and pp. 184-191, Maruzen Co., Ltd.; 16 pgs.

Encyclopedia of Chemistry 3, edited by Editorial Committee of Encyclopedia of Chemistry, Kyoritsu Shuppan Co., Ltd., Sep. 30, 1960, 1st Edition, 1st printing, pp. 312-313; 2 pgs.

Trent, D., et al—"Reactive stripping in a rotating packed bed for the production of hypochlorous acid", 1999, BHR Group Conference Series Publication, vol. 38 (Process Intensification for the Chemical Industry), pp. 217-231; 15 pgs.

Vajda, M., et al—"Membrane-Based Extraction Joined with Membrane-Based Stripping in a Circulating Arrangement II. Extraction of Organis Acids", 2003, Chemical Papers, vol. 57, Issue No. 1, pp. 3-10; 9 pgs.

Demarquay, M.—"De la Glycerine de ses Applications a la Chirurgie et a la Medecine", 1863, Librairie de la Faculte de Medecine, Paris, France; 26 pgs; no English translation provided. Best copy available.

Perry'S Chemical Engineers' Handbook, Sixth Edition—"Process Control. Temperature Measurements", 1984, McGraw Hill Inc., Section 22, pp. 22-32-22-37; 8 pgs; Best copy available.

Perry'S Chemical Engineers' Handbook, Sixth Edition—"Mass Transfer and Gas Absorption", 1984, McGraw Hill Inc., Section 14, pp. 14-1-14-40; 42 pgs; Best copy available.

U.S. Appl. No. 13/813,348, filed Jan. 30, 2012, Patrick Gilbeau, et al.
U.S. Appl. No. 13/818,753, fild Feb. 25, 2013, Patrick Gilbeau, et al.

Kaszonyi A. et al., "Bioglycerol a new platform chemical", in 44th International Petroleum Conference, 2009, 8 p., Bratislava, Slovak Republic.

Williamson R. et al., "DE-FC36-03GO1300 Final Report: Continuous Isosorbide Production from Sorbitol using Solid Acid Catalysis", 2006, 9 p., DOE Award for Iowa Corn Promotion Board.

Malhotra S. V. et al., "Applications of Corn-Based Chemistry", in The Bridge Publication of the National Academy of Engineering, 2007, V 34, No. 4, 8 p.

Jaffe M. et al., "Corn (Sugars) Based Chemistries for the Polymer Industry", in ANTEC 2009, 67th Annual Technical Conf., Proceed., Society of Plastic Engineers, Jun. 22-24, Mc Cormick, Place West Chigaco, Illinois.
Anon., "Iowa Corn Promotion Board, Njit to License Breakthrough, Safe Bio-Plastic Alternative", New Jersey Science & Technology University press release, Aug. 6, 2008.
Anon., "NJIT Patent May Be Able to Replace BPA; Make Consumer Products Safer", New Jersey Science & Technology University press release, Feb. 4, 2010.
Fenouillot F. et al, "Polymers from renewable 1,4:3,6-dianhydrohexitols (isosorbide isomannide and isoidide): A Review", in Progress in Polymer Science, 2010, V 35, N 5, p. 578-622.
U.S. Appl. No. 13/755,236, filed Jan. 31, 2013, Krafft, et al.
U.S. Appl. No. 13/709,218, filed Dec. 10, 2012, Boulos, et al.
U.S. Appl. No. 13/832,363, filed Mar. 15, 2013, Krafft, et al.
U.S. Appl. No. 13/876,003, filed Mar. 26, 2013, Gilbeau, et al.
Medium and Long-term Opportunities and Risks of the Biotechnological Production of Bulk Chemicals from renewable Resources—The Potential of White Technology—The BREW project—Final Report—prepared under the European Commission GRXTH Programme (DG Research) Ulrecht, Sep. 2006 (pp. 29-31).
Ullmann's Encyclopedia Industrial Chemistry, $5^{th}$ Ed. vol. A6 (1988) pp. 401-477.
Polymer Science Dictionary, M.S.M., Elsevier Applied Chemistry, London & New York, 1989 p. 86.
Perry's Chemical Engineers' Handbook, $6^{th}$ Edition, Section 21, pp. 21-55.
M. Schellentrager, "Untersuchungen zur oxidation Entfarbung aus gewahlter Reaktivfarbstoffe: Analyse der Abbauprodukte misteels hochauflosender LC-MS", Dissertation, XP 0002548413 (Jan. 1, 2006)w/ English Abstract.
E. Milchert et al., "Installation for the Recovery of Dichloropropanols and Epichlorohydrin from the Waste Water in Epichlorohydrin Production", Pol. J. Appl. Chem., vol. 41, p. 113-118 (1997).
Kleiboehmer W., et al, Solvay Werk Rheinberg; Integrierte Prozesse Separierte Abwasserbehandlungen—Gewaesserschutz, Wasser, Abwasser 200 (Wissenschaftlich-technische Mitteilungen des Instituts Zur Foerderung der Wasserguerte- und Wassermengenwirtschaft e; V;—2005 p. 81/-8/5., vol. 5.
Klaus Weissermel, et al., "Industrial Organic Chemistry," ($3^{rd}$ Completely Revised Edition); VCH 1997. p. 93-98.
Klaus Weissermel, et al., "Industrial Organic Chemistry," ($3^{rd}$ Completely Revised Edition); VCH 1997. p. 276-277.
Klaus Weissermel, et al., "Industrial Organic Chemistry," ($3^{rd}$ Completely Revised Edition); VCH 1997. p. 347-355.
Ying Ling Liu, "Epoxy Resins from Novel Monomers with a Bis-(9,10-dihydro-9-oxa-10-oxide-10-phosphaphenanthrene-10-yl-) Substituent," Journal of Polymer Science: Part A: Polymer Chemistry, vol. 40, 359-368 (2002).
Ying Ling Liu, "Phosphorous-Containing Epoxy Resins from a Novel Synthesis Route," Journal of Applied Polymer Science, vol. 83, 1697-1701 (2002).
[Unknown Author], Kirk Othmer Encyclopedia of Chemical Technology—vol. 2, p. 156, John Wiley and Sons, 1992.
Herman A. Bruson, et al., "Thermal Decomposition of Glyceryl Carbonates," Journal of the American Chemical Society, vol. 74, Apr. 1952 pp. 2100-2101.
Perry's Chemical Engineers Handbook 7th Ed., 11th Section, 1997, pp. 11.1-11.118 (submitted into two parts).
Perry's Chemical Engineers Handbook 7th Ed., 13th Section, 1997, pp. 13.1-13.108.
Perry's Chemical Engineers Handbook 7th Ed., 15th Section, 1997, pp. 15.1-15.47.
Ullmann's Encyclopedia of Industrial Chemistry 5th Ed., vol. A23, 1993, pp. 635-636.
Ullmann's Encyclopedia of Industrial Chemistry 5th Ed., vol. A13, 1989, p. 289.
Ullmann's Encyclopedia of Industrial Chemistry 5th Ed., vol. A11, 1988, pp. 354-360.

Attached certified Application No. FR 06.05325 filed Jun. 14, 2006 by Solvay S.A.-priority document to EP2007/55742 published as WO 2007/144335 (attached herein) 17 pgs.
Attached certified Application No. FR 07.53863 filed Mar. 15, 2007 by Solvay S.A. and published as FR2913683, 19 pgs (attached herein)-priority document to EP2007/55742 published as WO2007/144335 29 pgs (attached herein).
Gibson, "The preparation, properties, and uses of glycerol derivatives, Part III. The Chlorohydrins", 1931, Chemistry and Industry, Chemical Society, pp. 949-975.
Carre et al, 1931, "La transformation des alcools polyatomiques en mono-et en polychlorohydrines au moyen du chlorure de thionyle", Bulletin De La Societe Chimique De France, Societe Francaise De Chimie. Paris—ISSN 0037-8968, vol. 49, No. 49, pp. 1150-1154.
Fauconner, 1888, "Preparation de l'epichlorhydrine", Bull. Soc. Chim. FR, No. 50, pp. 212-214 (with enclosed translation in English).
Ullmann's Encyclopedia of Industrial Chemistry, "Industrially important epoxides", 1987, Fifth Completely Revised Edition, vol. A9, pp. 539-540.
Bonner et al, "The composition of constant boiling hydrochloric acid at pressures of 50 to 1220 millimeters", 1930, Journal of American Chemical Society, vol. 52, pp. 633-635.
Muskof et al, "Epoxy Resins" in Ullmann's Encyclopedia of Industrial Chemistry, 1987, 5th Ed., vol. A9, pp. 547-563.
Novelli, A., "The preparation of mono-and dichlorohydrins of glycerol", 1930, Anales Farmacia Bioquimica, vol. 1, pp. 8-19 (with English abstract).
Derwent Publications, AN 109:6092 CA, JP 62-242638, Oct. 23, 1987, 1 pg.
Derwent Publications, AN 1987-338139 [48], JP 62-242638, Oct. 23, 1987, 1 pg.
I. Miyakawa et al, Nagoya Sangyo Kagaku Kenkyusho Kenkyu Hokoku, 10, 49-52 (1957). (Abstract in English only). 1 pg.
Han Xiu-Ying et al, Shanxi Daxue Xuebao Bianjibu, 2002, 25(4), 379-80. (Abstract in English only), 1 pg.
Semendyaeva et al, 1981. Khimicheskaya Promyshlennost, Seriya: Khomaya Promyshlennost, 5. 21-2 (CA Summary). XP 002465275, 1 pg.
Rudnenko, EV, et al., 1988, Lakokrasochnye Materialy i lkh Primenenie, 4 69-71 (CA Summary) XP 002465276, 1 pg.
Kirk-Othmer Encyclopedia of Chemical Technology, 1978, 3rd Ed., vol. 4, Blood, Coagulants and Anticoagulants to Cardiovascular Agents. p. 847-848.
Jeffrey Lutje Spelberg, et al, A Tandem Enzyme Reaction to Produce Optically Active Halohydrins, Epoxides and Diols, Tetrahedron: Asymmetry, Elsevier Science Publishers, vol. 10, No. 15, 1999, pp. 2863-2870.
Oleoline.com. Glycerine Market report, Sep. 10, 2003, No. 62, 31 pgs.
Notification Under Act. No. 100/2001, Coll. as Amended by Act No. 93/2004, Coll. To the extent of Annex No. 4 (SPOLEK) Nov. 30, 2004, 80 pgs.
Documentation Under Act. No. 100/2001 Coll. as Amended by Act. No. 93/2004 Coll in the scope of appendix No. 4 (SPOLEK) Jan. 11, 2005, 86 pgs.
K. Weissermel & H.J. Arpe, Industrial Organic Chemistry, Third, Completely Revised Edition, VCH, 1997, pp. 149 & 275.
Industrial Bioproducts: "Today and Tomorrow." Energetics, Inc. for the U.S. Department of Energy, Office of Energy Efficiency and Renewable Energy, Office of the Biomass Program, Jul. 2003, pp. 49, 52 to 56.
Kirk Othmer Encyclopedia of Chemical Technology, Fourth Edition, 1992, vol. 2, p. 156, John Wiley & Sons, Inc.
Ullmann's Encyclopedia of Industrial Chemistry, Fifth, Completely Revised Edition, 1988, vol. A13, pp. 292-293.
The Merck Index, Eleventh Edition, 1989, pp. 759-760.
Ullmann's Encyclopedia of Industrial Chemistry, Fifth completely Revised Edition, vol. A1, 1985, pp. 427-429.
Ullmann's Encyclopedia of Industrial Chemistry, Fifth Completely Revised Edition, vol. A6, 1986, pp. 240-252.
Hancock, E.G., Propylene and its Industrial Derivatives, 1973, pp. 298-332.

K. Weissermel & H.J. Arpe, Industrial Organic Chemistry, Third, Completely Revised Edition, VCH 1997, pp. 149-163.

K. Weissermel & H.J. Arpe, in Industrial Organic Chemistry, Third, Completely Revised Edition, VCH 1997, pp. 275-276.

Robert T. Morrison & Robert N. Boyd, Organic Chemistry, 5th Ed., vol. II, pp. 666 to 667 and 712 to 714 (Japanese Translation), published on Jul. 10, 1970, Tokyo Kagaku Dozin Co., Ltd. (and copies of similar passages but retrieved from the English Fifth Edition of the Book, 1987).

Perry's Chemical Engineers' Handbook, Sixth Edition, Robert H. Perry, Don Green, 1984, Section 21-64 to 21-68.

Iwanami et al, Dictionary of Physics and Chemistry, Third Edition, Ryo Midorikawa /Iwanami Shoten, Publishers, May 29, 1971, pp. 270-271, 595 and 726.

Expert Opinion on the Environment Impact Assessment Documentation Pursuant to Annex No. 5 of Act No. 100/2001 Coll., as amended by later regulations of the project/intent combined process for the manufacture of epichlorohydrin (SPOLEK) Apr. 2005.

Kirk Othmer Encyclopedia of Chemical Technology, Third Edition, vol. 12, 1980, pp. 1002-1005.

Chemical Engineering Handbook, the 6th Edition, Edited by the Society of Chemical Engineers, published by Maruzen Co, Ltd., 1999, pp. 1296-1306 Pub. Feb. 25, 1999 w/English translation of p. 1296, Table 28.4, p. 1298, left column, lines 4-13 and p. 1305, Table 28.10.

Product Brochure of De Dietrich Company, Apr. 1996, pp. 3, 8 and 9 w/English translation of p. 8, left column, lines 1-4, p. 9.

The Journal of the American Chemical Society, vol. XLV, Jul.-Dec. 1923, pp. 2771-2772.

Berichte Der Deutschen Chemischen Gesellschaft, 1891, vol. 24, pp. 508-510.

Catalogue of Nittetu Chemical Engineering Ltd. (Published in Mar. 1994).

12093 Chemicals, The Chemical Daily Co., Ltd. (Published on Jan. 22, 1993) with attached English translation of relevant excerpts, 24 pgs.

Chemicals Guide, Chemical Daily Co., Ltd. (Published on Jun. 15, 1990) with attached English translation of relevant excerpts.

Horsley, Lee H.—"Azeotropic Data-III", The Dow Chemical Co., Midland, MI, American Chemical Society 1973; pp. 1-4; 4 pgs.

Suzawa, Yoshikazu, et al—"Incineration System for Waste Liquid Containing Chlorinated Organic Compounds", Chemical Apparatuses, 1981, vol. 23, No. 11; 34 pgs; Translation in English provided.

D'Alonzo, R.P., et al—"Glyceride Composition of Processed Fats and Oils As Determined by Glass Capillary Gas Chromatography", Journal of American Oil Chemists' Society, 1982, vol. 59, No. 7, pp. 292-295; 4 pgs.

Chemical Engineering Handbook, $6^{th}$ Revised Edition, 2001, pp. 1-36; 56 pgs; Translation in English provided.

"Electrolytic cell test for electrolysis of epoxy sewage salt to prepare chlor-alkali", Process Equipment Department of Research Institute of Chloro-Alkali, Shengyang Chemical Plant, Liaoning Chemical Industry, Issue n°2, pp. 32-37, published Dec. 31, 1981; 17 pgs; Translation in English provided.

Chengxin, Ren, et al—"Analysis on the Composition of the Byproduct During the Manufacturing Process of S-Epichlorohydrin by GC-MS", Chemical Analysis and Meterage, 2003, vol. 12, Issue No. 3, pp. 25-26; 6 pgs; Translation in English provided.

Encyclopedia of Chemical Technology, vol. 5, Nov. 1993; 6 pgs; Translation in English provided.

"Manufacture and use of epoxy resin", edited by Shanghai Resin Factory, published by China Petrochemical Press, First Edition, Oct. 1974; 16 pgs; Translation in English provided.

Gilman, Henry, et al—"Organic synthesis", Part 1, published by Scientific Publishing, 1957 (with abstract); 4 pgs.

Handbook of Chemical Products, Heavy Organic Chemicals, Second edition, published by Chemical Industry Press, Jan. 1995; 13 pgs; Translation in English provided.

Kiseleva, R. A., et al—"Study of the Interaction of Dibasic Acids with Glycerol", J. App. Chem. USSR, 1971, vol. 44, pp. 2086-2090; 5 pgs.

Handbook of Corrosion Data and Material Selection, published by Chemical Industry Press, edited by Jingyi Zuo, Yu Zuo; First edition, Oct. 1995, 5 pgs; Translation in English provided.

Handbook of Azeotropic Mixture, edited by Information Department of Comprehensive Scientific Technology Research Institution of Fushun City, 1993; 8 pgs; Translation in English provided.

"Industry Chemical Reaction and Application", published by Chinese Scientific Technology University Press, 1999; 4 pgs; Translation in English provided.

"Epoxy resin", published by Shanghai People's Publishing House, 1971; Translation in English provided; 21 pgs.

Boschan, Robert, et al—"The Role of Neighboring Groups in Replacement Reactions. XXI. Front-side Participation of Acetoxy Group. Catalytic Effect of Acetic Acid on the Reaction of Glycols with Hydrogen Chloride", Journal of the American Chemical Society, 1956, vol. 78, pp. 4921-4925; 5 pgs.

Encyclopedia for Chinese Adult Education, 1994, p. 623; 10 pgs; Translation in English provided.

RD 436092, Aug. 10, 2000.

Ullmann's Encyclopedia of Industrial Chemistry, 2005, "pH Measurement and Control", Wiley-VCH GmbH & Co. KGaA, Weinheim, 10.1002/14356007.e19_e01; pp. 1-31 (32 pgs).

U.S. Appl. No. 13/878,429, filed Apr. 9, 2013, Balthasart, et al.

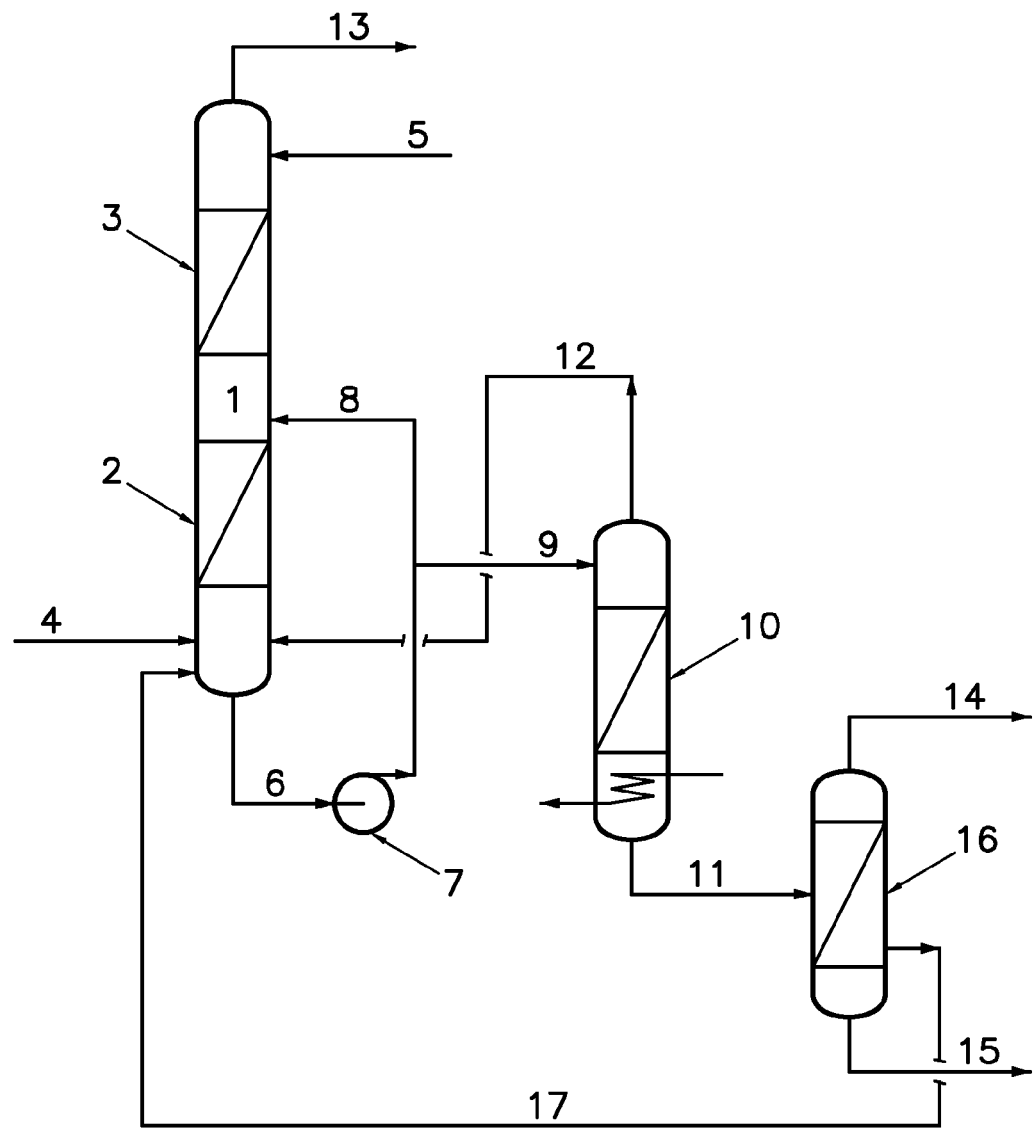

PROCESS FOR PURIFYING HYDROGEN CHLORIDE

The present patent application is a U.S. national stage entry under 35 U.S.C. §371 of International Application No. PCT/EP2009/061812 filed Sep. 11, 2009, which claims the benefit of the following French patent application FR 08.56138 filed on Sep. 2, 2008, the content of which is incorporated herein by reference for all purposes.

The present invention relates to a process for purifying hydrogen chloride (HCl). It relates more particularly to a process for purifying hydrogen chloride gas that contains aromatic organic compounds, in particular chlorinated aromatic compounds. It also relates to a process for manufacturing a chlorohydrin by hydrochlorination of a polyhydroxylated aliphatic hydrocarbon, using the hydrogen chloride obtained via the purification process according to the invention. It also relates to a process for manufacturing an epoxide by dehydrochlorination of the chlorohydrin obtained, and also to processes for manufacturing products derived from the epoxide.

A large number of industrial chemical processes generate hydrogen chloride, especially hydrogen chloride gas, as a by-product. Mention may be made, from among the most commonly practised, of the production of vinyl chloride, the production of chloromethanes and chlorinated solvents, the molecule of which contains at least two carbon atoms, the synthesis of isocyanates and the synthesis of fluorinated hydrocarbons.

This production of large quantities of hydrogen chloride raises the problem of its purification when it must be re-used as a raw material for other processes.

When the hydrogen chloride originates from processes for the manufacture of diisocyanates, toluene diisocyanate, 4,4'-diphenylmethane diisocyanate or hexamethylene-1,6-diisocyanate for example, this hydrogen chloride is contaminated with aromatic organic compounds, such as monochlorobenzene and dichlorobenzenes.

Thus, concerning the production of epichlorohydrin, it has been found that the synthesis process via alkaline dehydrochlorination of dichloropropanol obtained by hydrochlorination of glycerol necessitates using, in the hydrochlorination step, a hydrogen chloride that has previously been purified if it is desired to prevent contaminants of the hydrogen chloride from occurring in the epichlorohydrin and the products derived from the latter.

The processes for purifying hydrogen chloride proposed in the prior art have some disadvantages.

Solvent scrubbing processes, such as that mentioned in French patent 1417388, have the drawback that the compound used for the scrubbing in turn contaminates the hydrogen chloride and that the disposal of this compound raises a problem associated with the fact that the hydrogen chloride is still at least partially soluble in the liquid phase of said compound.

Another process for purifying hydrogen chloride, which can be used as a reactant in an ethylene oxychlorination step, by scrubbing with 1,2-dichloroethane is mentioned in document FR 2 881 732.

The processes that make use of fractional distillation including a condensation step, of adsorption or absorption by suitable liquids or solids, and of catalytic hydrogenation or oxidation reactions, as mentioned in document EP-B-0 774 450, have drawbacks associated sometimes with the complexity of the apparatus to be used, sometimes with the need to regenerate the adsorbents or absorbents used, loaded in turn with the impurities present in the hydrogen chloride to be purified, or else with the need to regenerate the costly hydrogenation or oxidation catalysts used.

Processes which consist in converting hydrogen chloride gas to hydrochloric acid and in then bringing this hydrochloric acid into contact with an anion exchange resin, as described in document EP-A-0 618 170, constitute complicated and costly solutions.

Purification processes that rest on a two-stage condensation with recycling of the coldest condensed phase from the second stage to the first, as described in document US-A-2004/016411, make use of complex devices comprising a costly refrigeration unit requiring high energy consumption. Furthermore, the efficiency of this type of purification is limited by the vapour pressure of the compounds to be removed, at the temperature reached at condensation.

The present invention aims to provide a process for purifying hydrogen chloride that does not have these drawbacks.

The present invention hence relates in a first aspect to a process for purifying hydrogen chloride, comprising at least one step of bringing said hydrogen chloride into contact with a scrubbing agent containing at least one chlorohydrin.

The hydrogen chloride may be in the form of a liquid, a gas, an aqueous solution or a combination of at least two of these forms. The hydrogen chloride is often in the gaseous state.

The hydrogen chloride may contain various types of impurities. These impurities may be organic compounds, inorganic compounds, or mixtures of them. The hydrogen chloride often contains organic compounds, and frequently aromatic organic compounds.

The impurity content of the hydrogen chloride is generally greater than or equal to 100 ppm by weight, usually greater than or equal to 1000 ppm by weight and often greater than or equal to 10 000 ppm by weight. This content is usually less than or equal to 10% by weight, frequently less than or equal to 5% by weight and in a lot of cases less than or equal to 2% by weight.

The process according to the invention preferably applies to the purification of hydrogen chloride resulting from syntheses involving the presence of aromatic organic compounds. On account of this origin, this hydrogen chloride contains, as impurities, one or more aromatic organic compounds, the standard boiling point of which is generally above 100° C., compounds that are at least partially soluble in the scrubbing agent or miscible therewith. Preferably, the hydrogen chloride to be purified is the by-product of the manufacture of organic isocyanates. More preferably, the hydrogen chloride to be purified is the by-product of the manufacture of organic isocyanates by reacting phosgene with an organic amine, usually an aromatic amine and preferably an aromatic diamine. In this particular case, the impurities are most frequently chloroaromatic compounds, typically monochlorobenzene and dichlorobenzene, used as solvents in this manufacture. The dichlorobenzene may be chosen from 1,2-dichlorobenzene, 1,3-dichlorobenzene, 1,4-dichlorobenzene, and mixture of at least two of these isomers.

The chloroaromatic impurity content of the hydrogen chloride is generally greater than or equal to 100 ppm by weight, usually greater than or equal to 1000 ppm by weight and often greater than or equal to 10 000 ppm by weight. This content is usually less than or equal to 10% by weight, frequently less than or equal to 5% by weight and in a lot of cases less than or equal to 2% by weight.

In the present description, the expression "scrubbing agent containing at least one chlorohydrin" or more simply "scrubbing agent" is understood to mean a composition in which at least one portion of the chlorohydrin is present in the liquid state.

The scrubbing agent that can be used according to the present invention often contains at least one chlorohydrin mainly in the liquid state.

The expression "chlorohydrin" is used here to describe a compound containing at least one hydroxyl group and at least one chlorine atom attached to various saturated carbon atoms. The chlorohydrins may be chosen from chloroethanol, chloropropanol, chloropropanediol, dichloropropanol and mixtures of at least two of them. The chlorohydrins are generally chosen from monochloropropanediol, dichloropropanol, and mixtures thereof. Monochloropropanediol is often used. Dichloropropanol is very suitable. The chlorohydrins that are more particularly encountered are chosen from 2-chloroethanol, 1-chloropropane-2-ol, 2-chloropropane-1-ol, 1-chloropropane-3-ol, 1-chloropropane-2,3-diol, 2-chloropropane-1,3-diol, 1,3-dichloropropane-2-ol, 2,3-dichloropropane-1-ol, chlorohydrins of polyglycerol such as the diglycerol of linear or cyclic structure, and mixtures of at least two of them. The chlorohydrins that are often encountered are diglycerol monochlorohydrin, diglycerol dichlorohydrin, diglycerol trichlorohydrin, 1-chloropropane-2,3-diol, 2-chloropropane-1,3-diol, and mixtures of at least two of them. Chlorohydrins that are frequently encountered are 1,3-dichloropropane-2-ol, 2,3-dichloropropane-1-ol, and mixtures thereof.

The presence, in said scrubbing agent, of other compounds capable of solubilizing the impurity (impurities) present in the hydrogen chloride to be purified or of forming a liquid mixture with it (them) is not at all excluded from the context of the invention.

The content of chlorohydrin in the scrubbing agent is generally greater than or equal to 100 g of chlorohydrin per kg of scrubbing agent, usually greater than or equal to 200 g/kg, habitually greater than or equal to 300 g/kg, in a lot of cases greater than or equal to 400 g/kg and often greater than or equal to 500 g/kg. This content is generally less than or equal to 950 g/kg, often less than or equal to 900 g/kg, frequently less than or equal to 800 g/kg and in a lot of cases less than or equal to 700 g/kg.

The content of chlorohydrin in the scrubbing agent may also be greater than or equal to 950 g/kg, sometimes greater than or equal to 990 g/kg and in certain cases greater than or equal to 999 g/kg. A scrubbing agent composed mainly of at least one chlorohydrin is very suitable. A scrubbing agent composed mainly of dichloropropanol is very particularly suitable.

Most particularly, the scrubbing agent is substantially composed of chlorohydrin in the liquid state, more specifically in the case where the hydrogen chloride to be purified is intended to be used in a process for the hydrochlorination of a polyhydroxylated aliphatic hydrocarbon, intended to produce a chlorohydrin. In this case, an essential advantage of the process of the invention lies in the fact that the presence of this chlorohydrin is in no way troublesome, since it is a compound formed during this hydrochlorination.

The scrubbing agent according to the invention may additionally contain at least one compound chosen from water, alcohols, aldehydes, ketones, carboxylic acids, carboxylic acid esters, ethers, halogenated hydrocarbons, epoxides, metals, in the metallic state or in the salt state, and mixtures of at least two of them. The chlorohydrins are not considered to be alcohols or halogenated hydrocarbons or ethers or esters. This case is encountered often when the scrubbing agent originates from the purge of a process for the manufacture of a chlorohydrin by hydrochlorination of a polyhydroxylated aliphatic hydrocarbon.

The content of water in the scrubbing agent is generally greater than or equal to 0.01 g/kg, usually greater than or equal to 0.1 g/kg, commonly greater than or equal to 1 g/kg, often greater than or equal to 5 g/kg, frequently greater than or equal to 10 g/kg, and particularly greater than or equal to 20 g/kg. This water content is generally less than or equal to 300 g/kg, usually less than or equal to 200 g/kg, commonly less than or equal to 150 g/kg, often less than or equal to 100 g/kg, frequently less than or equal to 70 g/kg and particularly less than or equal to 50 g/kg.

The alcohols may be chosen from monoalcohols, diols, polyols other than diols, and mixtures of at least two of them.

The monoalcohols may be chosen from 2-propanol, allyl alcohol, chloroethanols, often 2-chloroethanol, chloropropanols, often 3-chloro-1-propanol, chloropropenols, often 2-chloropropenol, phenol, and mixtures of at least two of them.

The content of monoalcohol in the scrubbing agent is generally greater than or equal to 0.001 g/kg, usually greater than or equal to 0.005 g/kg, commonly greater than or equal to 0.01 g/kg, often greater than or equal to 0.02 g/kg, frequently greater than or equal to 0.04 g/kg, and particularly greater than or equal to 0.05 g/kg. This monoalcohol content is generally less than or equal to 20 g/kg, usually less than or equal to 10 g/kg, commonly less than or equal to 5 g/kg, often less than or equal to 2 g/kg, frequently less than or equal to 1 g/kg and particularly less than or equal to 0.1 g/kg.

The diols may be chosen from 1,3-propanediol, 1,2-propanediol, butanediol, and mixtures of at least two of them.

The content of diol in the scrubbing agent is generally greater than or equal to 0.001 g/kg, usually greater than or equal to 0.005 g/kg and frequently greater than or equal to 0.01 g/kg. This diol content is generally less than or equal to 40 g/kg, usually less than or equal to 20 g/kg, commonly less than or equal to 10 g/kg, often less than or equal to 5 g/kg, frequently less than or equal to 1 g/kg and particularly less than or equal to 0.5 g/kg.

An example of a polyol other than a diol is glycerol.

The content of polyol other than a diol in the scrubbing agent is generally greater than or equal to 0.001 g/kg, usually greater than or equal to 0.01 g/kg, commonly greater than or equal to 0.1 g/kg, often greater than or equal to 1 g/kg, frequently greater than or equal to 2 g/kg, and particularly greater than or equal to 5 g/kg. This content of polyol other than a diol is generally less than or equal to 100 g/kg, usually less than or equal to 80 g/kg, commonly less than or equal to 60 g/kg, often less than or equal to 50 g/kg, frequently less than or equal to 20 g/kg and particularly less than or equal to 10 g/kg.

The aldehydes may be chosen from acetaldehyde, acrolein, and mixtures thereof.

The content of aldehyde in the scrubbing agent is generally greater than or equal to 0.001 g/kg, usually greater than or equal to 0.005 g/kg, commonly greater than or equal to 0.01 g/kg, often greater than or equal to 0.015 g/kg, frequently greater than or equal to 0.02 g/kg, and particularly greater than or equal to 0.05 g/kg. This aldehyde content is generally less than or equal to 10 g/kg, usually less than or equal to 5 g/kg, commonly less than or equal to 2 g/kg, often less than or equal to 1 g/kg, frequently less than or equal to 0.5 g/kg and particularly less than or equal to 0.1 g/kg.

The ketones may be chosen from acetone, butanones, often 2-butanone, hydroxyacetone, chloroacetone, pentanediones, often 2,3-pentanedione, cyclopentanone, methylcyclopentenones, often 2-methyl-2-cyclopentene-1-one, and mixtures of at least two of them.

The content of ketone in the scrubbing agent is generally greater than or equal to 0.001 g/kg, usually greater than or equal to 0.005 g/kg, commonly greater than or equal to 0.01 g/kg, often greater than or equal to 0.05 g/kg, frequently greater than or equal to 0.1 g/kg, and particularly greater than or equal to 0.5 g/kg. This ketone content is generally less than or equal to 10 g/kg, usually less than or equal to 8 g/kg, commonly less than or equal to 6 g/kg, often less than or equal to 4 g/kg, frequently less than or equal to 2 g/kg and particularly less than or equal to 1 g/kg.

The carboxylic acids may be chosen from monocarboxylic acids, polycarboxylic acids, often dicarboxylic acids, and mixtures of at least two of them. Acetic acid is an example of a monocarboxylic acid. Adipic acid is an example of a dicarboxylic acid.

The content of carboxylic acid in the scrubbing agent is generally greater than or equal to 0.001 g/kg, usually greater than or equal to 0.01 g/kg, commonly greater than or equal to 0.1 g/kg, often greater than or equal to 0.5 g/kg, frequently greater than or equal to 1 g/kg, and particularly greater than or equal to 5 g/kg. This carboxylic acid content is generally less than or equal to 100 g/kg, usually less than or equal to 80 g/kg, commonly less than or equal to 60 g/kg, often less than or equal to 40 g/kg, frequently less than or equal to 20 g/kg and particularly less than or equal to 10 g/kg.

The carboxylic acid esters may be chosen from the esters of the aforementioned acids with chlorohydrins and alcohols. In particular, these esters may be chosen from the adipates of glycerol, of diglycerol, of monochloropropanediol, of dichloropropanol, and mixtures of at least two of them.

The content of carboxylic acid ester in the scrubbing agent is generally greater than or equal to 0.01 g/kg, usually greater than or equal to 0.1 g/kg, commonly greater than or equal to 1 g/kg, often greater than or equal to 5 g/kg, frequently greater than or equal to 10 g/kg, and particularly greater than or equal to 15 g/kg. This carboxylic acid ester content is generally less than or equal to 500 g/kg, usually less than or equal to 300 g/kg, commonly less than or equal to 150 g/kg, often less than or equal to 100 g/kg, frequently less than or equal to 50 g/kg and particularly less than or equal to 20 g/kg.

The halogenated hydrocarbons may be chosen from monochloropropanes, often 2-chloropropane, monochloropropenes, often allyl chloride, dichloropropanes, often 1,3-dichloropropane, dichloropropenes, often cis-1,3-dichloropropene, frequently trans-1,3-dichloropropene, trichloropropanes, often 1,2,3-trichloropropane, chlorobromopropanes, and mixtures of at least two of them.

The content of halogenated hydrocarbons in the scrubbing agent is generally greater than or equal to 0.001 g/kg, usually greater than or equal to 0.005 g/kg, commonly greater than or equal to 0.01 g/kg, often greater than or equal to 0.05 g/kg, frequently greater than or equal to 0.1 g/kg, and particularly greater than or equal to 0.5 g/kg. This halogenated hydrocarbon content is generally less than or equal to 20 g/kg, usually less than or equal to 10 g/kg, commonly less than or equal to 5 g/kg, often less than or equal to 3 g/kg, frequently less than or equal to 2 g/kg and particularly less than or equal to 1 g/kg.

Epichlorohydrin is an example of an epoxide.

The content of epoxide in the scrubbing agent is generally greater than or equal to 0.001 g/kg, usually greater than or equal to 0.005 g/kg, commonly greater than or equal to 0.01 g/kg, often greater than or equal to 0.05 g/kg, frequently greater than or equal to 0.1 g/kg, and particularly greater than or equal to 0.5 g/kg. This epoxide content is generally less than or equal to 10 g/kg, usually less than or equal to 8 g/kg, commonly less than or equal to 6 g/kg, often less than or equal to 4 g/kg, frequently less than or equal to 2 g/kg and particularly less than or equal to 1 g/kg.

The ethers may be chosen from polyglycerols, often diglycerols, frequently diglycerols of linear structure or of cyclic structure, and mixtures thereof.

The content of ethers in the scrubbing agent is generally greater than or equal to 0.005 g/kg, usually greater than or equal to 0.01 g/kg, commonly greater than or equal to 0.05 g/kg, often greater than or equal to 0.1 g/kg, frequently greater than or equal to 0.5 g/kg, and particularly greater than or equal to 1 g/kg. This ether content is generally less than or equal to 50 g/kg, usually less than or equal to 40 g/kg, commonly less than or equal to 30 g/kg, often less than or equal to 20 g/kg, frequently less than or equal to 10 g/kg and particularly less than or equal to 5 g/kg.

The metals in the metallic state or in the salt state may be chosen from iron, nickel, chromium, calcium, sodium, and mixtures of at least two of them.

The content of metals in the metallic state or in the salt state, expressed as elemental metal, in the scrubbing agent is generally greater than or equal to 0.001 g/kg, usually greater than or equal to 0.005 g/kg, commonly greater than or equal to 0.01 g/kg, often greater than or equal to 0.05 g/kg, frequently greater than or equal to 0.1 g/kg, and particularly greater than or equal to 0.5 g/kg. This metal content is generally less than or equal to 20 g/kg, usually less than or equal to 15 g/kg, commonly less than or equal to 10 g/kg, often less than or equal to 5 g/kg, frequently less than or equal to 2 g/kg and particularly less than or equal to 1 g/kg.

The metals may be present in the form of metal salts. These salts may be organic or inorganic salts. The expression "inorganic salts" is understood to mean salts for which the constituent ions do not contain a carbon-carbon bond or a carbon-hydrogen bond. The expression "organic salts" is understood to mean salts for which at least one of the constituent ions contains at least one carbon-carbon bond or one carbon-hydrogen bond. The metal salts may be chosen from metal chlorides, sulphates, hydrogensulphates, hydroxides, carbonates, hydrogencarbonates, phosphates, hydrogenphosphates, nitrates or borates, and mixtures of at least two of them.

The various impurities may advantageously be present in the hydrogen chloride in the form of droplets, solid particles or gaseous fractions.

The process according to the invention is advantageously carried out at any pressure compatible with keeping at least one portion of the hydrogen chloride to be purified in the gaseous state, often compatible with keeping the hydrogen chloride to be purified entirely in the gaseous state. This pressure is generally greater than or equal to 1 bar and often greater than or equal to 5 bar. This pressure is usually less than or equal to 20 bar and frequently less than or equal to 15 bar. A pressure in the vicinity of 10 bar is very suitable.

The temperature at which the process is carried out may be easily chosen by a person skilled in the art in order to promote the dissolution and/or absorption of the impurities in the scrubbing agent and taking account of the vapour pressure values of the aromatic organic compounds present as impurities in the hydrogen chloride to be purified. This temperature is generally greater than or equal to 10° C., often greater than or equal to 20° C., frequently greater than or equal to 50° C. and in a lot of cases greater than 75° C. This temperature is customarily less than or equal to 120° C., often less than or equal to 100° C. and sometimes less than 90° C. Values close to ambient temperature (about 25° C.) are very suitable, for example in the case where the scrubbing agent is mainly composed of chlorohydrin, such as dichloropropanol. Values close to 80° C. are very suitable, for example when the scrubbing agent originates from the purge of a process for the manufacture of a chlorohydrin by hydrochlorination of a polyhydroxylated aliphatic hydrocarbon.

The ratio between the respective flows of scrubbing agent and hydrogen chloride to be purified is not critical and can vary to a large extent. It is in practice limited only by the cost of the possible regeneration of the scrubbing agent. The flow of scrubbing agent, expressed as a weight percentage relative to the flow of hydrogen chloride to be purified, is generally greater than or equal to 0.5, often greater than or equal to 1 and frequently greater than or equal to 2. This flow is usually less than or equal to 50, frequently less than or equal to 20 and often less than or equal to 10.

The ratio between the respective quantities of scrubbing agent and hydrogen chloride to be purified is not critical and can vary to a large extent. It is in practice limited only by the cost of the possible regeneration of the scrubbing agent. The quantity of scrubbing agent, expressed as a weight percentage relative to the quantity of hydrogen chloride to be purified, is generally greater than or equal to 0.5, often greater than or equal to 1, frequently greater than or equal to 2, and in particular greater than or equal to 10. This quantity is usually less than or equal to 80, frequently less than or equal to 60, often less than or equal to 40 and in particular less than or equal to 20.

The contacting step of the process according to the invention may be carried out in continuous mode, semi-continuous mode or batch mode. The expression "continuous mode" is understood to denote an operating mode which is continuous for the gas phase and continuous for the liquid phase. The expression "semi-continuous mode" is understood to denote an operating mode which is continuous for the gas phase and in batch mode for the liquid phase. The expression "batch mode" is understood to denote an operating mode which is in batch mode for the gas phase and in batch mode for the liquid phase. It is preferred to operate in semi-continuous or continuous mode. Continuous mode is preferred.

When the process is carried out in batch mode, the duration of the contacting step between the scrubbing agent and the hydrogen chloride to be purified is generally greater than or equal to 0.01 min, often greater than or equal to 0.02 min and frequently greater than or equal to 0.05 min. This duration is usually less than or equal to 60 min, commonly less than or equal to 40 min, and frequently less than or equal to 20 min.

When the process is carried out in continuous mode, the residence time of the gas phase during the contacting step between the scrubbing agent and the hydrogen chloride to be purified is generally greater than or equal to 1 s, often greater than or equal to 2 s and frequently greater than or equal to 3 s. This residence time is usually less than or equal to 120 s, commonly less than or equal to 90 s, and frequently less than or equal to 60 s.

When the process is carried out in continuous mode, the residence time of the liquid phase during the contacting step between the scrubbing agent and the hydrogen chloride to be purified is generally greater than or equal to 10 s, often greater than or equal to 15 s and frequently greater than or equal to 20 s. This residence time is usually less than or equal to 60 min, commonly less than or equal to 50 min, and frequently less than or equal to 45 min.

When the process is carried out in semi-continuous mode, the residence time of the gas phase during the contacting step between the scrubbing agent and the hydrogen chloride to be purified is generally greater than or equal to 1 s, often greater than or equal to 2 s and frequently greater than or equal to 3 s. This residence time is usually less than or equal to 120 s, commonly less than or equal to 90 s, and frequently less than or equal to 60 s.

The proportion of impurities present in the hydrogen chloride to be purified before the step of contacting with the scrubbing agent, and which is found in the scrubbing agent at the end of this step, is generally greater than or equal to 50%, in many cases greater than or equal than 60%, commonly greater than or equal than 70%, often greater than or equal than 80%, usually greater than or equal to 90%, frequently greater than or equal to 99%, more often greater than or equal to 99.99% and in a lot of cases greater than or equal to 99.999%.

The process according to the invention comprises at least one step of bringing the hydrogen chloride into contact with the scrubbing agent. Preferably, and in the case of operating moreover in continuous mode, the process is however carried out in two steps; one of the steps thus comprises loop flow (recycling) of the scrubbing agent and the other step comprises a supply of fresh scrubbing agent. In this case, the flow of fresh scrubbing agent, expressed as a weight percentage of the flow of hydrogen chloride to be purified, is generally greater than or equal to 0.1, often greater than or equal to 1 and frequently greater than or equal to 3. This flow is commonly less than or equal to 20, often less than or equal to 10, and in a lot of cases less than or equal to 7. Such a flow in the vicinity of 5 percent by weight is very suitable.

The liquid mixture or the solution (referred to as fraction (f) below) comprising the scrubbing agent, loaded with the impurities extracted from the hydrogen chloride to be purified, and also the portion of this hydrogen chloride that is dissolved in or mixed with the said scrubbing agent, may then be treated, at least partly, by any known means, especially to separate the hydrogen chloride therefrom, and/or the impurities extracted, for example, by scrubbing, by neutralization, by settling, by filtration of the "dead end filtration" type, of the "cross filtration" type, or by means of membranes, such as ceramic membranes for example, by distillation, by absorption, by stripping, etc. The treatment may be carried out by one or by a combination of at least two of these means. The particular implementation of one of these means may be carried out in one or more devices; in particular when it is a stripping, settling or filtration treatment. In the case of a stripping treatment, the treatment may be carried out in one or more stripping columns, often in several columns and frequently in two columns.

It is preferable to separate the hydrogen chloride from the scrubbing agent loaded with impurities by subjecting all or at least part of the fraction (f) to a stripping operation. Preferably, only part of the fraction (f) is subjected to a stripping operation. For this purpose, the fraction (f) is advantageously divided into a liquid fraction (f1) and a liquid fraction (f2). This division may be carried out using any device known for separating a liquid stream into two and for regulating the resulting flows, such as a tee fitting equipped with flow control valves, for example. In the case where the purification process according to the invention is carried out in continuous mode, the fraction (f1) is then advantageously recycled to the step of contacting the hydrogen chloride with the scrubbing agent. The fraction (f2) (also referred to as the "purge stream") is itself advantageously subjected to the stripping operation mentioned above, during which operation, on the one hand, the hydrogen chloride contained in this fraction (f2)—which may be recycled to the step of contacting with the scrubbing agent—and, on the other hand, the remainder of the purge stream essentially comprising the residue of the scrubbing agent loaded with impurities and referred to below as the residual purge stream, are separated.

In a first embodiment where the scrubbing agent is substantially composed of chlorohydrin in the liquid state, this residual purge stream may advantageously be reused by conveying it to a unit in which the chlorohydrin, the contaminants with boiling points below that of the chlorohydrin and the contaminants with boiling points above that of the chlorohydrin are separated by distillation. The chlorohydrin obtained may be used for any purpose, preferably it is subjected to a dehydrochlorination reaction in order to produce an epoxide.

In a second embodiment where the scrubbing agent is substantially composed of a purge stream from a process for the hydrochlorination of a polyhydroxylated hydrocarbon, in the liquid state, this residual purge stream may advantageously be reused by conveying it to a unit in which a high-temperature oxidation is carried out. The hydrocarbon-based content of the purge stream is reused in the form of energy and the chlorocarbon-based content of the purge stream is converted to hydrogen chloride. This hydrogen chloride may be reused in the form of an aqueous solution of hydrogen chloride or returned to the step of contacting with the scrubbing agent.

In a third embodiment where the scrubbing agent is substantially composed of a purge stream from a process for the hydrochlorination of a polyhydroxylated hydrocarbon, in the liquid state, the purge stream (f2) may advantageously be reused by conveying it to a unit in which a high-temperature oxidation is carried out. The hydrocarbon-based content of the purge stream is reused in the form of energy and the chlorocarbon-based content of the purge stream is converted to hydrogen chloride. This hydrogen chloride may be reused in the form of an aqueous solution of hydrogen chloride or returned to the step of contacting with the scrubbing agent. In this case, the purge stream (f2) is not first subjected to the stripping operation.

The respective proportions of the mass flow of the fraction (f2) to the mass flow of supply of fresh scrubbing agent is generally greater than or equal to 50%, often greater than or equal to 60% and frequently greater than or equal to 70%. This ratio is generally less than or equal to 500%, often less than or equal to 200%, frequently less than or equal to 160% and in a lot of cases less than or equal to 140%.

The purification process according to the invention is highly efficient.

The proportion of aromatic organic impurities present in the hydrogen chloride to be purified before the step of contacting with the scrubbing agent, and which is found in the scrubbing agent at the end of this step is generally greater than or equal to 50%, in many cases greater than or equal to 60%, commonly greater than or equal to 70%, often greater than or equal to 80%, usually greater than or equal to 90%, frequently greater than or equal to 99%, often greater than or equal to 99.99% and in a lot of cases greater than or equal to 99.999%.

This process makes it possible to reduce the level of aromatic organic impurities in the purified hydrogen chloride, commonly to less than 500 ppm generally to less than 100 ppm by weight, usually to less than 50 ppm, in many cases to less than 25 ppm, often to less than 10 ppm, frequently to less than 5 ppm and specifically to less than 1 ppm and particularly to less than 0.5 ppm. This level is generally greater than or equal to 1 ppb. In the case of the chloroaromatic compounds mentioned above, it is possible to attain, by virtue of the process according to the invention, a residual content in the purified hydrogen chloride that does not exceed 10 ppm.

The process according to the invention has the advantage of making it possible to prevent the contamination, by impurities present in the hydrogen chloride, of products resulting from a manufacture that uses hydrogen chloride.

The step of bringing the hydrogen chloride into contact with the scrubbing agent may be carried out in any type of device, in particular the devices intended for the contacting of gases and liquids. Devices of this type are described in "Perry's Chemical Engineers' Handbook", Sixth Edition, McGraw Hill Inc., 1984, Section 18.

These devices may be made from or covered with any type of material, such as for example, carbon steel, non-impregnated graphite, and polymeric materials such as polyester.

These devices are generally made from or covered with materials that are resistant to corrosion, under the conditions of the hydrogen chloride purification step. These materials may be chosen from enamelled steel, metal alloys, metals, polymers, impregnated graphite, non-impregnated graphite, refractory materials, ceramics, cermets, phenolic resins and epoxy resins.

The metal alloys are often Ni—Mo alloys, such as Hastelloy B2 for example.

The metals may be chosen from tantalum, gold, silver, molybdenum and nickel, preferably from tantalum and molybdenum, most particularly preferably the metal is tantalum.

The polymers are often chosen from polyolefins, fluoropolymers and sulphur-containing polymers.

The polyolefins are preferably chosen from polypropylene and polyethylene, preferably polypropylene.

The fluoropolymers may be completely or partially fluorinated. A partially fluorinated polymer is polyvinylidene fluoride. The perfluoropolymers are often chosen from polytetrafluoroethylene, poly(perfluoropropylvinyl ether) and copolymers of tetrafluoroethylene and hexafluoropropylene.

The impregnated graphite may be chosen from graphite impregnated with phenolic resins or with polytetrafluoroethylene.

The preferred materials are preferably chosen from enamelled steel, tantalum, perfluoropolymers, phenolic resins and impregnated graphite.

According to one particular aspect, the equipment for purifying hydrogen chloride, in particular hydrogen chloride gas, comprises at least one scrubbing column with countercurrent flow, on the one hand, of the hydrogen chloride to be purified and, on the other hand, of the scrubbing agent defined above, said scrubbing column comprising two sections placed one on top of the other. The purified hydrogen chloride gas escapes at the top of the column. At the base of the column, a fraction (f) is collected that comprises the scrubbing agent, the impurities (as defined above) extracted from the hydrogen chloride to be purified and the portion of this hydrogen chloride that is dissolved in or mixed with the scrubbing agent.

In the scrubbing column that comprises two sections, the first section is advantageously supplied with at least part of the fraction (f) defined above, withdrawn at the base of this section and recycled in a loop. This fraction (f) may advantageously be treated, during its recycling, fully or partially, by any means known for this purpose, in order to separate therefrom the scrubbing agent loaded with the impurities that it has extracted from the hydrogen chloride. These means may be those mentioned above in connection with the treatment of the fraction (f). The fraction (f) is preferably treated, at least partly, in at least one stripping column, in order to extract the impurities therefrom, before being recycled to the top of the first section of the scrubbing column.

In the scrubbing column that comprises two sections, the second section, surmounting the first, is advantageously supplied with fresh scrubbing agent.

The scrubbing column may be equipped with any known type of packing material that promotes exchanges between the component in the gas state to be purified (hydrogen chloride) and the liquid scrubbing agent. An inorganic packing may advantageously be used, in particular, a packing made of stoneware, ceramic, graphite or metal carbide, preferably made of stoneware or ceramic. A description of the most commonly used materials appears, for example, in paragraphs 3.4., 3.5. and 3.6. from pages 8-20 and 8-21 of volume B 3: Unit Operations II of Ullmann's Encyclopedia of Industrial Chemistry, Fifth Completely Revised Edition, published by VCH, 1988. As examples of stoneware or ceramic packing, mention may be made of Raschig rings, Berl saddles, Intalox saddles, ceramic catalyst supports such as Macro Trap type supports and Denstone type supports. In the scrubbing column that comprises two sections, a packing made up of Raschig rings or Berl saddles has been found to be advantageous, with a very particular preference for Berl saddles, in the first section, considering the often quite high liquid flow rate passing through this section. The second section, which only receives the supplementary scrubbing agent, may advantageously be equipped with bubble trays that ensure very good contact of the liquid and gas phases.

The invention also relates in a second aspect to a process for the hydrochlorination of a polyhydroxylated aliphatic hydrocarbon, of an ester of a polyhydroxylated aliphatic hydrocarbon, or of a mixture of the two, to chlorohydrin, using the hydrogen chloride obtained by the purification process according to the invention.

More specifically, the invention also relates to a process for manufacturing a chlorohydrin via reaction between a polyhydroxylated aliphatic hydrocarbon, an ester of a polyhydroxylated aliphatic hydrocarbon, or a mixture of the two, and a chlorinating agent comprising the hydrogen chloride obtained by the purification process according to the invention.

The expression "polyhydroxylated aliphatic hydrocarbon" relates to a hydrocarbon that contains at least two hydroxyl groups attached to two different saturated carbon atoms. The polyhydroxylated aliphatic hydrocarbon may contain, but is not limited to, 2 to 60 carbon atoms.

Each of the carbons of a polyhydroxylated aliphatic hydrocarbon bearing the functional hydroxyl (OH) group cannot possess more than one OH group, and must be of sp3 hybridization. The carbon atom bearing the OH group may be primary, secondary or tertiary. The polyhydroxylated aliphatic hydrocarbon used in the present invention must contain at least two carbon atoms of sp3 hybridization bearing an OH group. The polyhydroxylated aliphatic hydrocarbon includes any hydrocarbon that contains a vicinal diol (1,2-diol) or a vicinal triol (1,2,3-triol) including higher orders of these vicinal or adjacent repeat units. The definition of the polyhydroxylated aliphatic hydrocarbon also includes, for example, one or more 1,3-, 1,4-, 1,5- and 1,6-diol functional groups. The polyhydroxylated aliphatic hydrocarbon may also be a polymer such as polyvinyl alcohol. Geminal diols, for example, are excluded from this class of polyhydroxylated aliphatic hydrocarbons.

The polyhydroxylated aliphatic hydrocarbons may contain aromatic entities or heteroatoms including, for example, heteroatoms of halogen, sulphur, phosphorus, nitrogen, oxygen, silicon and boron type, and mixtures thereof.

Polyhydroxylated aliphatic hydrocarbons that can be used in the present invention include, for example, 1,2-ethanediol (ethylene glycol), 1,2-propanediol (propylene glycol), 1,3-propanediol, 1-chloro-2,3-propanediol (chloropropanediol), 2-chloro-1,3-propanediol (chloropropanediol), 1,4-butanediol, 1,5-pentanediol, cyclohexanediols, 1,2-butanediol, 1,2-cyclohexanedimethanol, 1,2,3-propanetriol (also known as "glycerol" or "glycerine"), and mixtures thereof. Preferably, the polyhydroxylated aliphatic hydrocarbon used in the present invention includes, for example, 1,2-ethanediol, 1,2-propanediol, 1,3-propanediol, chloropropanediol and 1,2,3-propanetriol, and mixtures of at least two of them. More preferably, the polyhydroxylated aliphatic hydrocarbon used in the present invention includes, for example, 1,2-ethanediol, 1,2-propanediol, chloropropanediol and 1,2,3-propanetriol, and mixtures of at least two of them. 1,2,3-propanetriol or glycerol is the most preferable.

The esters of the polyhydroxylated aliphatic hydrocarbon may be present in the polyhydroxylated aliphatic hydrocarbon and/or be produced in the chlorohydrin manufacturing process and/or be manufactured prior to the chlorohydrin manufacturing process. Examples of esters of the polyhydroxylated aliphatic hydrocarbon include ethylene glycol monoacetate, propanediol monoacetates, glycerol monoacetates, glycerol monostearates, glycerol diacetates and mixtures thereof.

The term "chlorohydrin" is defined above. A chlorohydrin that contains at least two hydroxyl groups is also a polyhydroxylated aliphatic hydrocarbon. Therefore, in the hydrochlorination process according to the invention, the starting material and the product of the reaction may each be chlorohydrins. In this case, the chlorohydrin "product" is more chlorinated than the initial chlorohydrin, that is to say that it has more chlorine atoms and fewer hydroxyl groups than the initial chlorohydrin.

In one very suitable embodiment, the chlorohydrin is dichloropropanol and the hydrogen chloride is purified by being brought into contact with a scrubbing agent that contains dichloropropanol, often by being brought into contact with a scrubbing agent essentially composed of dichloropropanol and the purified hydrogen chloride is intended to be used in a dichloropropanol manufacturing process in which glycerol is reacted with a chlorinating agent that contains this purified hydrogen chloride.

In another embodiment which is also very suitable, the hydrogen chloride is purified by being brought into contact with a scrubbing agent that contains a purge stream from said dichloropropanol manufacturing process, often by being brought into contact with a scrubbing agent essentially composed of this purge stream.

This purge stream typically comprises, per kg, from 150 to 650 g of monochloropropanediol, from 1 to 70 g of glycerol, from 50 to 350 g of dichloropropanol, at most 100 g of water, from 25 to 130 g of diglycerol dichlorohydrin, from 5 to 25 g of diglycerol monochlorohydrin, and from 20 to 200 g of monochloropropanediol esters. The reaction between the polyhydroxylated aliphatic hydrocarbon and the chlorinating agent containing the purified hydrogen chloride may be carried out under temperature, pressure, duration and residence time conditions as described in Application WO 2005/054167 by SOLVAY SA, from page 8, line 25, to page 10, line 10, the content of which is incorporated here by reference.

In a preferred variant of the second aspect, the invention relates to a process for the hydrochlorination of glycerol, of an ester of glycerol, or of a mixture of the two, to dichloropropanol, using the hydrogen chloride obtained by the purification process according to the invention.

In that variant, the glycerol generally contains nitrogen compounds, usually at least one nitrogen compound, as described in Application WO 2009/077528 in the name of SOLVAY SA, from page 1, line 31, to page 3, line 24, and the content of which is incorporated here by reference. The nitrogen compounds can be organic nitrogen compounds or inorganic nitrogen compounds.

The organic nitrogen compounds can be those present in cell of plant origin. They are often selected from the group consisting of amines, urea, proteins, peptides, amino-acids, nucleic acids, glucosinolates, degradation products thereof like isothiocyanates, thiocyanates, nitriles, oxazolidinethiones, phospholipids containing nitrogen, chlorophylls, pheophytines, sinapine, and any mixture of at least two of them.

Examples of phospholipids containing nitrogen are phospatidyl cholin, phosphatidyl serin and phosphatidyl ethanolamine.

Examples of amino acids free or which could be part of peptides or proteins composition are alanine, arginine, aspartic acid, cystine, glutamic acid, glycine, histidine, isoleucine, leucine, lysine, methionine, phenylalanine, proline, serine, threonine, tryptophane, tyrosine, valine and any mixture of at least two of them.

Examples of glucosinolates are sinigrine, gluconapine, glucobrassicanapine, glycorucine, gluconasturtiine, glucoraphanin, glucoalyssin, gluconasturtiine, progoitrine, napoleiferine, glucobrassicine, neoglucobrassicine, and any mixture of at least two of them.

The inorganic nitrogen compounds are frequently selected from the groups consisting of ammonia, hydrazine, chloramines, ammonium inorganic salts, nitrates, nitrites, cyanates, isocyanates, ammonium isothiocyanates, metallic isothiocyanates, and any mixture of at least two of them.

The total nitrogen content of the glycerol expressed as g of N/kg is generally greater than or equal to 0.001, usually greater than or equal to 0.005, often greater than or equal to 0.01, and more often greater than or equal to 0.5. That content is generally lower than or equal to 5, frequently lower than or equal to 2, and more frequently lower than or equal to 1.

That nitrogen content is obtained by chemiluminescence technique.

In that variant, the glycerol generally contains sulfur compounds. The sulfur compounds can be organic sulfur compounds or inorganic sulfur compounds.

Examples of organic sulfur compounds are amino acids containing sulfur, like methionine, cysteine, and cystine, free or being part of peptides or proteins composition, glucosinolates, degradation products thereof like isothiocyanates and thiocyanates, and any mixture of at least two of them.

Examples of inorganic sulfur compounds are sulfates, hydrogensulfates, sulfites, hydrogensulfites, sulfides, hydrogensulfides containing compounds, and any mixture of least two of them. The inorganic sulfur compound is often a sulfate containing compound.

The total sulfur content of the glycerol expressed as g of S/kg is usually greater than or equal to 0.0001, often greater than or equal to 0.001, and more often greater than or equal to 0.01. That content is generally lower than or equal to 15, frequently lower than or equal to 10, more frequently lower than or equal to 5 and still more frequently lower than or equal to 1.

In that variant, the glycerol generally contains phosphorus compounds.

The phosphorus compounds can be organic phosphorus compounds or inorganic phosphorus compounds.

Examples of organic phosphorus compounds are glycerophospholids, like phosphatidyl choline, phosphatidylethanolamine, phosphatidylserine, phosphatidylinositol, polyphosphoinositides, phosphatidylglycerol, phosphatidic acid, and any mixture of at least two of them.

Examples of inorganic phosphorus compounds are phosphate, hydrogenphosphates, phosphite and hydrogenphosphites containing compounds, and mixture thereof. The inorganic sulfur compound is often a phosphate containing compound.

The total phosphorus content of the glycerol expressed as g of P/kg is generally greater than or equal to 0.00001, more generally greater than or equal to 0.0001, usually greater than or equal to 0.001, often greater than or equal to 0.01, and more often greater than or equal to 0.5. That content is generally lower than or equal to 20, frequently lower than or equal to 15, more frequently lower than or equal to 10, and still more frequently lower than or equal to 5, and yet more frequently lower than or equal to 1.

In that variant, the glycerol generally contains inorganic chlorine compounds.

Examples of inorganic chlorine compounds are chloride containing compounds.

The total inorganic chlorine content of the glycerol expressed as g of chloride/kg is generally greater than or equal to 0.001, is usually greater than or equal to 0.05, often greater than or equal to 0.1, and more often greater than or equal to 0.5. That content is generally lower than or equal to 40, frequently lower than or equal to 20, more frequently lower than or equal to 10, and still more frequently lower than or equal to 5, and yet more frequently lower than or equal to 1.

In that variant, the glycerol may also comprise monoalcohols, usually at least one monoalcohol, such as the monoalcohols described in Application WO 2007/144335 in the name of SOLVAY SA, from page 3, lines 26 to 31, and the content of which is incorporated here by reference.

Examples of monoalcohols are methanol, ethanol, propanol, allyl alcohol, butanol, pentanol, hexanol, heptanol, octanol, methylpropanol, 3-methylbutane-1-ol, 2-methylbutane-1-ol, pentenol, hexenol, 2-phenylethanol, and any mixture of at least two of them.

The monoalcohol content of the glycerol expressed as g of methanol/kg of glycerol is usually greater than or equal to 0.001, often greater than or equal to 0.01, more often greater than or equal to 0.1, yet more often greater than or equal to 0.5, still more often greater than or equal to 1 and in particular greater than or equal to 10. That content is generally lower than or equal to 500, frequently lower than or equal to 300, more frequently lower than or equal to 200, yet more frequently lower than or equal to 100 and still more frequently lower than or equal to 50. The monoalcohol is often chosen from the group consisting of methanol, ethanol, n-propanol, isopropanol, n-butanol, and any mixture of at least two of them.

In that variant, the glycerol generally contains diols, usually at least one diol, as described in Application WO 2009/000773 in the name of SOLVAY SA, from page 1, line 30, to page 3, line 21, and the content of which is incorporated here by reference.

Examples of diols are 1,2-ethanediol (ethylene glycol), 1,2-propanediol (propylene glycol), 1,3-propanediol, 1,2-butanediol, 2,3-butanediol, 1,4-butanediol and any mixture of at least two of them.

The diol content of the glycerol expressed as g of diol/kg of glycerol is usually greater than or equal to 0.001, often greater than or equal to 0.01, more often greater than or equal to 0.1 and yet more often greater than or equal to 0.5. That content is generally lower than or equal to 10, frequently lower than or equal to 5, and more frequently lower than or equal to 1. The diol is frequentely selected from the group consisting of ethylene glycol, 1,2-propanediol, 1,3-propanediol, 1,2-butanediol, 1,3-butanediol, 2,3-butanediol, and any mixture of at least two of them.

In that variant, the glycerol generally contains glycerol alkyl ethers, usually at least one glycerol alkyl ether, as described in Application WO 2007/144335 in the name of SOLVAY SA, from page 1, line 33, to page 3, line 25, and the content of which is incorporated here by reference.

Examples of glycerol alkyl ethers are mono-, di- and tri-ethers of glycerol the alkyl groups of which are independently selected from the group consisting of methyl, ethyl, propyl, butyl, pentyl, hexyl, heptyl and octyl groups.

The glycerol alkyl ether content of the glycerol expressed as g of glycerol alkyl ether/kg of glycerol is usually greater than or equal to 0.001, often greater than or equal to 0.01, more often greater than or equal to 0.1, yet more often greater than or equal to 0.5 and still more often greater than or equal to 1. That content is generally lower than or equal to 15, frequently lower than or equal to 10, and more frequently lower than or equal to 5. The glycerol alkyl ether is often chosen from 3-methoxy-1,2-propanediol, 2-methoxy-1,3-propanediol, 3-monopropylenediol or any mixture of at least two of them.

In that variant, the glycerol may have an alkali metal and/or alkaline earth metal content as described in WO 2006/100315 of SOLVAY SA, the content of which is incorporated herein by reference, and especially the passages from page 7, line 11, to page 9, line 10.

In that variant, the glycerol may contain elements other than alkali metals and alkaline earth metals as described in WO 2006/100319 of SOLVAY SA, the content of which is incorporated herein by reference, especially the passages from page 2, line 3 to 8, and from page 6, line 20, to page 9, line 14.

In that variant, the glycerol may also comprise metals, often at least one metal. The metal can be present in the metallic form, as a salt, or as a mixture thereof. The metal is often found in the elements of the groups IA, IIA, IVB, VB, VIB, VIIB, VIIII, IB, IIB, IIA, IVA, VA, VIA of the Periodic Table of the Elements.

The metal of Group IA content of the glycerol expressed as mg of metal/kg of glycerol is usually greater than or equal to 0.01, often greater than or equal to 0.1, more often greater than or equal to 1, yet more often greater than or equal to 10, still more often greater than or equal to 100 and in particular greater than or equal to 500. That content expressed as g of metal/kg of glycerol is generally lower than or equal to 50, usually lower than or equal to 30, frequently lower than or equal to 10, and more frequently lower than or equal to 5 and yet more frequently lower than or equal to 1. The metal of Group IA is often found in the group consisting of group consisting of Na, K, and mixture thereof.

The metal of Group IIA content of the glycerol expressed as mg of metal/kg of glycerol is usually greater than or equal to 0.001, often greater than or equal to 0.005, more often greater than or equal to 0.01, yet more often greater than or equal to 0.05, still more often greater than or equal to 0.1 and in particular greater than or equal to 1. That content is generally lower than or equal to 200, frequently lower than or equal to 150, and more frequently lower than or equal to 100, yet more frequently lower than or equal to 50, still more frequently lower than or equal to 10. The metal of Group IIA is often found in the group consisting of group consisting of Ba, Ca, Be, Mg and mixture thereof.

The metal of Group IVB content of the glycerol expressed as mg of metal/kg of glycerol is usually greater than or equal to 0.001, often greater than or equal to 0.005, more often greater than or equal to 0.01, and yet more often greater than or equal to 0.05. That content is generally lower than or equal to 10, frequently lower than or equal to 5, and more frequently lower than or equal to 1, and yet more frequently lower than or equal to 0.1. The metal of Group IVB is often Ti.

The metal of Group VB content of the glycerol expressed as mg of metal/kg of glycerol is usually greater than or equal to 0.001, often greater than or equal to 0.005, more often greater than or equal to 0.01, yet more often greater than or equal to 0.05. That content is generally lower than or equal to 10, frequently lower than or equal to 5, and more frequently lower than or equal to 1, and yet more frequently lower than or equal to 0.1. The metal of Group VB is often V.

The metal of Group VIB content of the glycerol expressed as mg of metal/kg of glycerol is usually greater than or equal to 0.0001, often greater than or equal to 0.001, more often greater than or equal to 0.01, yet more often greater than or equal to 0.05. That content is generally lower than or equal to 10, frequently lower than or equal to 5, and more frequently lower than or equal to 1, and yet more frequently lower than or equal to 0.1. The metal of Group VIB is often Cr.

The metal of Group VIIB content of the glycerol expressed as mg of metal/kg of glycerol is usually greater than or equal to 0.0001, often greater than or equal to 0.001, more often greater than or equal to 0.01, yet more often greater than or equal to 0.05. That content is generally lower than or equal to 10, frequently lower than or equal to 5, and more frequently lower than or equal to 1, and yet more frequently lower than or equal to 0.1. The metal of Group VIIB is often Mn.

The metal of Group VIII content of the glycerol expressed as mg of metal/kg of glycerol is usually greater than or equal to 0.0001, often greater than or equal to 0.001, more often greater than or equal to 0.01, yet more often greater than or equal to 0.05 and still more often greater than or equal to 0.1. That content is generally lower than or equal to 50, frequently lower than or equal to 30, more frequently lower than or equal to 20, yet more frequently lower than or equal to 10 and still more frequently lower than or equal to 1. The metal of Group VIII is often found in the group consisting of group consisting of Co, Fe, Ni, and mixture of at least two of them.

The metal of Group IB content of the glycerol expressed as mg of metal/kg of glycerol is usually greater than or equal to 0.0001, often greater than or equal to 0.001, more often greater than or equal to 0.01, yet more often greater than or equal to 0.05. That content is generally lower than or equal to 10, frequently lower than or equal to 5, and more frequently lower than or equal to 1, and yet more frequently lower than or equal to 0.1. The metal of Group IB is often Cu.

The metal of Group IIB content of the glycerol expressed as mg of metal/kg of glycerol is usually greater than or equal to 0.0001, often greater than or equal to 0.001, more often greater than or equal to 0.01, yet more often greater than or equal to 0.05. That content is generally lower than or equal to 10, frequently lower than or equal to 5, and more frequently lower than or equal to 1, and yet more frequently lower than or equal to 0.1. The metal of Group IIB is often found in the group consisting of group consisting of Cd, Hg, Zn, and any mixture of at least two of them.

The metal of Group IIIA content of the glycerol expressed as mg of metal/kg of glycerol is usually greater than or equal to 0.0001, often greater than or equal to 0.001, more often greater than or equal to 0.01, yet more often greater than or equal to 0.05. That content is generally lower than or equal to 10, frequently lower than or equal to 5, and more frequently lower than or equal to 1, and yet more frequently lower than or equal to 0.1. The metal of Group IIIA is often Al.

The metal of Group IVA content of the glycerol expressed as mg of metal/kg of glycerol is usually greater than or equal to 0.0001, often greater than or equal to 0.001, more often greater than or equal to 0.01, yet more often greater than or equal to 0.05. That content is generally lower than or equal to 10, frequently lower than or equal to 5, and more frequently lower than or equal to 1, and yet more frequently lower than or equal to 0.1. The metal of Group IVA is often found in the group consisting of group consisting of Pb, Sn, and mixture thereof.

The metal of Group VA content of the glycerol expressed as mg of metal/kg of glycerol is usually greater than or equal to 0.0001, often greater than or equal to 0.001, more often greater than or equal to 0.01, yet more often greater than or equal to 0.05. That content is generally lower than or equal to 1000, frequently lower than or equal to 500, and more frequently lower than or equal to 100, yet more frequently lower than or equal to 10, still more frequently lower than or equal to 1 and in particular lower than or equal to 0.1. The metal of Group VA is often found in the group consisting of group consisting of As, Sb, P, and any mixture of at least two of them.

The metal of Group IVA content of the glycerol expressed as mg of metal/kg of glycerol is usually greater than or equal to 0.0001, often greater than or equal to 0.001, more often greater than or equal to 0.01, yet more often greater than or equal to 0.05. That content is generally lower than or equal to 20, frequently lower than or equal to 10, more frequently lower than or equal to 1, and yet more frequently lower than or equal to 0.1. The metal of Group VIA is often found in the group consisting of group consisting of S, Se, Te, and any mixture of at least two of them.

In that variant, the glycerol may also comprise carboxylic acids, often at least one carboxylic acid.

The carboxylic is usually selected from the group consisting of acetic acid, propionic acid, butyric acid and any mixture of at least two of them.

The carboxylic acid can be a fatty acid. The fatty acid is generally selected from the group consisting of valeric, caproic, caprylic, caprique, lauric, myristic, palmitic, margaric, stearic, arachidic, behenic, lignoceric, hexacosanoic, octacosanoic, melissic, dotriacontanoic, alpha-linoleic, stearidonic, eicosapentanoic, docosahexenoic, linoleic, gamma-linolenic, dihomo-gamma-linolenic, arachidonic, myristoleic, palmitoleic, petrosenilic, oleic, vaccenic, gondoic, elaidic, erucic, nervonic, alpha-linolenic, eicosatrienoic, stearidonic, octadecapentaenoic, eicosatetraenoic, eicosapentaenoic, docosapentaenoic, docosahexaenoic, ricinoleic, and any mixture of at least two of them.

The carboxylic acid, preferably fatty acid, content of the glycerol expressed as g of carboxylic acid/kg of glycerol is usually greater than or equal to 0.001, often greater than or equal to 0.01, and more often greater than or equal to 0.1. That content is generally lower than or equal to 5, frequently lower than or equal to 3, more frequently lower than or equal to 2, and yet more frequently lower than or equal to 1. The fatty acid is often selected from the group consisting of palmitic acid, oleic acid, linoleic acid, stearic acid, and any mixture of at least two of them.

The carboxylic acid content of the glycerol expressed as mmol of carboxylic acid fonctionalities/kg is usually greater than or equal to 0.1, often greater than or equal to 0.2, and more often greater than or equal to 0.5. That content is generally lower than or equal to 50, frequently lower than or equal to 40, more frequently lower than or equal to 30, and still more frequently lower than or equal to 20, yet more frequently lower than or equal to 10 and in particular lower than or equal to 1.

In that variant, the glycerol may also comprise carboxylic acids salts, often at least one carboxylic acid salt. Those salts are usually metal salts of the aforementioned carboxylic acids. The metals salts are often found in the group consisting of Na, K, Ba, Ca, Be, Mg, Ti, V, Cr, Mn, Co, Fe, Ni, Cu, Cd, Hg, Zn, Al, Pb, Sn, As, Sb, and any mixture of at least two of them.

The carboxylic acid salt content of the glycerol expressed as g of carboxylate anion/kg is usually greater than or equal to 0.01, often greater than or equal to 0.05, and more often greater than or equal to 1. That content is generally lower than or equal to 80, frequently lower than or equal to 60, more frequently lower than or equal to 40, and still more frequently lower than or equal to 20, yet more frequently lower than or equal to 10 and in particular lower than or equal to 5. The carboxylic acid salt is often a salt of acetic acid.

The carboxylic acid salt content of the glycerol expressed as mmol of carboxylate anion functionalities/kg is usually greater than or equal to 1, often greater than or equal to 2, and more often greater than or equal to 10. That content is generally lower than or equal to 1000, frequently lower than or equal to 800, more frequently lower than or equal to 600, and still more frequently lower than or equal to 400, yet more frequently lower than or equal to 200 and in particular lower than or equal to 100.

In that variant, the glycerol may also comprise alkyl esters of fatty acids, usually at least one alkyl ester of fatty acids, glycerol esters, generally at least one glycerol ester, and salts, commonly at least one salt, as described in Application WO 2007/144335 in the name of SOLVAY SA, from page 5, lines 12 to 20.

The carboxylic acid ester content of the glycerol expressed as mmol of carboxylic acid ester fonctionalities/kg is usually greater than or equal to 0.1, often greater than or equal to 0.2, and more often greater than or equal to 0.5. That content is generally lower than or equal to 10, frequently lower than or equal to 5, and more frequently lower than or equal to 1.

The alkyl ester of fatty acid is usually an ester of fatty acid frequently selected from the group of the fatty acids aforementioned and with a monoalcohol, often selected from the group consisting of methanol, ethanol, propanol and any mixture of two of them.

The alkyl ester of fatty acid content of the glycerol expressed as g of alkyl ester of fatty acid/kg of glycerol is usually greater than or equal to 0.01, often greater than or equal to 0.05, and more often greater than or equal to 0.1. That content is generally lower than or equal to 10, frequently lower than or equal to 5, more frequently lower than or equal to 2, and yet more frequently lower than or equal to 1. The alkyl ester of fatty acid is often selected from the group consisting of methyl palmitate, methyl oleate, methyl linoleate, methyl linolenate, methyl stearate, and any mixture of at least two of them.

The glycerol ester is usually mono-, a di- or a triester of glycerol with a carboxylic acid frequently selected from the group of the carboxylic acids aforementioned, often selected from the group consisting acetic acid, propionic acid, fatty acids aforementioned and any mixture of two of them. The esters of glycerol with fatty acids more often encountered are monopalmitate, monooletae, monolinoleate, monolinolenate, monostearate, and any mixture of at least two of them.

The alkyl ester of fatty acid content of the glycerol expressed as g of alkyl ester of fatty acid/kg of glycerol is usually greater than or equal to 0.01, often greater than or equal to 0.05, and more often greater than or equal to 0.1. That content is generally lower than or equal to 10, frequently lower than or equal to 5, more frequently lower than or equal to 2, and yet more frequently lower than or equal to 1.

In that variant, the glycerol may be obtained starting from fossil raw materials or starting from renewable raw materials, preferably starting from renewable raw materials, as described in WO 2005/054167 of SOLVAY SA, the content of which is incorporated herein by reference, and especially the passages from page 1, line 26, to page 4, line 2

In that variant, the glycerol may also be obtained starting from fossil raw materials or starting from renewable raw materials, preferably starting from renewable raw materials, as described in WO 2009/000773 of SOLVAY SA, the content of which is incorporated herein by reference, and especially the passages at page 10, lines 16 to 23, and at page 11, lines 4 to 25.

In that variant, the glycerol contains generally an amount of heavy compounds other glycerol and whose boiling temperature under a pressure of 1 bar absolute is at least 15° C. greater than the boiling temperature of dichloropropanol as described in WO 2006/1000316 of SOLVAY SA the content of which is incorporated herein by reference, especially the passages from page 15, line 32, to page 17, line 33.

In that variant, the glycerol may contain glycerol oligomers as described in PCT/EP2009/053766 of SOLVAY SA the content of which is incorporated herein by reference, especially the passages from page 1, line 25, to page 6, line 19.

The glycerol oligomer is generally selected from the group consisting of diglycerol, cyclic diglycerol, polyglycerols containing more than 2 glycerol units, cyclic polyglycerol i.e. polyglycerols containing more than 2 glycerol units and at least one ring, and any mixture of at least two of them.

The diglycerol is often selected from the group consisting of 3-(2,3-dihydroxypropoxy)-propane-1,2-diol, 3-(2-hydroxy-1-hydroxymethylethoxy)propane-1,2-diol et 2-(2-hydroxy-1-hydroxymethylethoxy)propane-1,3-diol), and any mixture of at least two of them.

The cyclic diglycerol is often selected from the group consisting of cis- and trans-2,5-bis-(hydroxymethyl)-1,4-dioxane, cis- and trans-2,6-bis-(hydroxymethyl)-1,4-dioxane, cis- and trans-6-hydroxy-2-hydroxymethyl-1,4-dioxepane, et cis- and trans-3,7-dihydroxy-1,5-dioxocane, and any mixture of at least two of them.

The polyglycerol is often selected from the group consisting of triglycerol, tetraglycerol, pentaglycerol, hexaglycerol, heptaglycerol, octaglycerol, and any mixture of at least two of them.

The glycerol oligomer content of the glycerol expressed as g of glycerol oligomer/kg of glycerol is usually greater than or equal to 0.01, often greater than or equal to 0.05, and more often greater than or equal to 0.1. That content is generally lower than or equal to 10, frequently lower than or equal to 5, more frequently lower than or equal to 2, and yet more frequently lower than or equal to 1. The glycerol oligomer is often selected from the group consisting of diglycerol, cyclic diglycerol, preferably aforementioned, and any mixture of at least two of them.

In that variant, the glycerol may contain aldehydes. The aldehydes are often selected from the group consisting of formaldehyde, acetaldehyde, propionaldehyde, butyraldehyde, pentanal, hexanal, heptanal, octanal, nonanal, decanal, undecanal, methylbutanal, glyceraldehyde, acrolein, pentenal, hexenal, hexadienal, heptenal, pyruvaldehyde, benzaldehyde, 2-hydroxy-propionaldéhyde, 3-hydroxy-propionaldéhyde, and any mixture of at least two of them.

The aldehyde content of the glycerol expressed as g of aldehyde/l of glycerol is usually greater than or equal to 0.01, often greater than or equal to 0.05, and more often greater than or equal to 0.1. That content is generally lower than or equal to 10, frequently lower than or equal to 5, more frequently lower than or equal to 2, and yet more frequently lower than or equal to 1. The aldehydes often encountered is glyceraldehyde.

In that variant, the glycerol may contain ketones. The ketones are often selected from the group consisting of acetone, butanone, pentanone, hexanone, heptanone, octanone, nonanone, decanone, undecanone, 2,3-butanedione, cyclopentanone, methylcyclopentenone, acetophenone, hydroxyacetone, dihydroxyacetone, and mixture thereof.

The ketone content of the glycerol expressed as g of ketone/l of glycerol is usually greater than or equal to 0.01, often greater than or equal to 0.05, and more often greater than or equal to 0.1. That content is generally lower than or equal to 10, frequently lower than or equal to 5, more frequently lower than or equal to 2, and yet more frequently lower than or equal to 1.

In that variant, the glycerol may comprise acetals and ketals of the aforementioned aldehydes and ketones with glycerol, such as for example acetol glycerol ketal, 3-hydroxy-propionaldehyde ketal, and mixtures thereof.

In that variant, the glycerol may comprise carotenoids, such as for example, phytoene, phytofluene, cis-beta-carotene, beta-carotene, alpha-carotenes, cis-alpha-carotene, z-carotene, d-carotene, g-carotene, neurosporene, alpha-zeacarotene, beta-zeacarotene, lycopene, and any mixture of at least two of them.

In that variant, the glycerol may comprise aromatic and heteroaromatic derivatives, such as for example, tocopherols (alpha, beta, gamma and delta), tocotrienol, plastochromanol, ubiquinone, furane, methyl-furanes, dimethylfuranes, propylfuranes, pentylmethylfurane, mono- and di-substituted thiophenes, naphtalene, ethylnaphtalene, dimethylnaphtalene, acenaphtene, phenanthrene, pyrene, fluoranthrene, benzanthracene, chrysene, perylene, methoxybenzene, dimethoxybenzene, phenols, phenolic acids, polyphenols, and any mixture of at least two of them.

In that variant, the glycerol may comprise sugar derivatives such as for example, monogalactosyldiacylglycerols, digalactosylglycerols, sterolglycosides, their hydrolysis products and any mixture of at least two of them.

In that variant, the glycerol may contain water.

The water content of the glycerol expressed as g of water/kg of glycerol is usually greater than or equal to 0.01, often greater than or equal to 0.05, and more often greater than or equal to 0.1. That content is generally lower than or equal to 200, frequently lower than or equal to 100, more frequently lower than or equal to 50, yet more frequently lower than or equal to 10, still more frequently lower than or equal to 5 and in particular lower than or equal to 1.

In that variant, the glycerol may exhibit an ash content expressed in weight percent, generally higher than of 0.01, often greater than or equal to 0.05, and more often greater than or equal to 0.1. That content is generally lower than or equal to 40, frequently lower than or equal to 20, more frequently lower than or equal to 10, yet more frequently lower than or equal to 5, and in particular lower than or equal to 1.

In that variant, the glycerol may exhibit a MONG (non glycerinous organic matter) content expressed in weight percent, generally higher than of 0.01, often greater than or equal to 0.05, and more often greater than or equal to 0.1. That content is generally lower than or equal to 80, frequently lower than or equal to 60, more frequently lower than or equal to 30, yet more frequently lower than or equal to 20, and in particular lower than or equal to 10.

In that variant, the glycerol may contain other compounds such n-alkanes linear, of formula $CH_3(CH_2)_xCH_3$, with and odd or even number of carbon atoms from 11 to 35, branched alkanes with and odd or even number of carbon atoms from 11 to 35, alkyl esters of formula $(CH_3(CH_2)_xCOO(CH_2)_yCH_3$, with an even number of carbon atoms from 34 to 62, fatty alcohols (primary) of formula $CH_3(CH_2)_yCH_2OH$ with an even number of carbon atoms from 22 to 32, fatty aldehydes of formula $CH_3(CH_2)_yCHO$ with an even number of carbon atoms from 22 to 32, ketones of formula $CH_3(CH_2)_xCO(CH_2)_yCH_3$ with an odd number of carbon atoms from 23 to 33, fatty alcohols (secondary) of formula $CH_3(CH_2)_xCHOH(CH_2)_yCH_3$ with an odd number of carbon atoms from 23 to 33, β-diketones of formula $CH_3(CH_2)_xCOCH_2CO(CH_2)_yCH_3$ with an odd number of carbon atoms from 27 to 33, triterpenols, sterols like cholesterol, campesterol, stigmasterol and sitosterol, α-amyrin, β-amyrin, uvaol, lupeol, erythrodiol, triterpenoid acids like ursolic acid, oleanolic acid, etc., hydroxy-β-diketones, oxo-β-diketones, alkenes (squalene), branched carboxylic acids, branched esters, acetates and benzoates of aliphatic alcohols, methyl, phenylethyl and triterpenoid esters, ceramides, and any mixture of at least two of them.

In that variant, the reaction between glycerol and the chlorinating agent the hydrogen chloride may be carried out in a reaction medium such described in WO 2006/106154 of SOLVAY SA, the content of which is incorporated herein by reference, especially the passages from page 14, line 15, to page 17, line 10.

In that variant, the reaction with the chlorinating agent may be carried out in the presence of a catalyst, preferably a carboxylic acid or a carboxylic acid derivative, as described in Patent Application WO 2005/054167, from page 6, line 24, to page 7, line 35 in the name of SOLVAY SA, the content of which is incorporated here by reference.

In that variant, the reaction with the chlorinating agent may be carried out for a catalyst concentration, at a temperature, at a pressure and at a residence time such described in WO 2005/054167 of SOLVAY SA, the content of which is incorporated herein by reference, especially the passages from page 8, line 1, to page 10, line 10.

In that variant, the reaction with the chlorinating agent may be carried out such described in WO 2007/054505 of SOLVAY SA, the content of which is incorporated herein by reference, especially the passages from page 1, line 24 to page 6, line 18.

In that variant, the process for manufacturing dichloropropanol may be carried in equipments made of or coated with materials which are resistant to the corrosion by the chlorinating agent under the process conditions, such as described in WO 2005/054167 of SOLVAY SA, the content of which is incorporated herein by reference, especially the passages from page 6, lines 3 to 23.

In that variant, the process for manufacturing dichloropropanol may be carried in equipments made of or coated with materials which are resistant to the corrosion by the chlorinating agent under the process conditions, such as described in WO 2006/100317 of SOLVAY SA, the content of which is incorporated herein by reference, especially the passages from page 23, line 22, to page 27, line 25.

In that variant, the process for manufacturing dichloropropanol according to the invention may be carried in equipments made of or coated with materials which are resistant to the corrosion by the chlorinating agent under the process conditions, such as described in WO 2009/043796 of SOLVAY SA, the content of which is incorporated herein by reference, especially the passages from page 1, line 30, to page 9, line 17, and from page 19, line 25, to page 20, line 33.

In that variant, the reaction with the chlorinating agent may be carried out under stirring with a stirring system such described in WO 2008/145729 of SOLVAY SA, the content of which is incorporated herein by reference, especially the passages from page 1, line 30, to page 2, line 33, and from page 6, line 22, to page 14, line 31.

In that variant, the reaction with the chlorinating agent may be carried out in a liquid reaction medium such described in WO 2006/106154 of SOLVAY SA, the content of which is incorporated herein by reference, especially the passages from page 1, line 29, to page 2, line 6, and from page 14, line 15, to page 17, line 10.

In that variant, the reaction with the chlorinating agent may be carried out in a reactor the feeding of which is described in WO 2008/107468 of SOLVAY SA, the content of which is incorporated herein by reference, especially the passages from page 1, line 29, to page 4, line 27, and from page 5, line 34, to page 9, line 17.

In that variant, a separation of the dichloropropanol from the other compounds of the reaction mixture may be carried out such described in WO 2005/054167 of SOLVAY SA, the content of which is incorporated herein by reference, especially the passages from page 12, line 1, to page 17, line 20.

In that variant, a separation of the dichloropropanol from the other compounds of the reaction mixture may be carried out according to methods such described in WO 2006/100313 of SOLVAY SA, the content of which is incorporated herein by reference, especially the passages at page 2, lines 1 to 23, and from page 21, line 7, to page 25, line 25.

In that variant, a separation of the dichloropropanol from the other compounds of the reaction mixture may be carried out according to methods such described in WO 2006/100314 of SOLVAY SA, the content of which is incorporated herein by reference, especially the passages at page 2, lines 6 to page 3, line 4, and from page 18, line 33, to page 22, line 29.

In that variant, a separation of the dichloropropanol from the other compounds of the reaction mixture may be carried out according to methods such described in WO 2006/100320 of SOLVAY SA, the content of which is incorporated herein by reference, especially the passages from page 1, line 30, to page 2, line 23, and from page 6, line 25, to page 10, line 28.

In that variant, a separation of the dichloropropanol from the other compounds of the reaction mixture may be carried out according to methods such described in WO 2006/100315 of SOLVAY SA, the content of which is incorporated herein by reference, especially the passages at page 2, lines 3 to 29, and from page 23, line 3, to page 24, line 13.

In that variant, a separation of the dichloropropanol from the other compounds of the reaction mixture may be carried out according to methods such described in WO 2008/110588 of SOLVAY SA, the content of which is incorporated herein by reference, especially the passages from page 1, line 31, to page 27, line 25.

In that variant, the dichloropropanol is generally obtained as a mixture of 1,3-dichloropropan-2-ol and 2,3-dichloropropan-1-ol isomers such described in WO 2006/100319 of SOLVAY SA, the content of which is incorporated herein by reference, especially the passages from page 23, line 34, to page 24, line 29.

In that variant, the dichloropropanol may contain halogenated ketones such described in WO 2006/100311 of SOLVAY SA, the content of which is incorporated herein by reference, especially the passages at page 2, lines 22 to 34, and from page 22, line 8, to page 23, line 35.

The invention also relates in a third aspect to a process for manufacturing an epoxide, comprising the process for manufacturing the chlorohydrin, in which the chlorohydrin obtained via reaction between the polyhydroxylated aliphatic hydrocarbon, the ester of the polyhydroxylated aliphatic hydrocarbon or the mixture of the two, and the chlorinating agent containing the purified hydrogen chloride, is subjected to a dehydro chlorination reaction, often in the presence of a basic agent.

The chlorohydrin may be chosen from chloroethanol, chloropropanol, chloropropanediol, dichloropropanol and mixtures of at least two of them. The chlorohydrin is often dichloropropanol.

The epoxide may be chosen from ethylene oxide, propylene oxide, glycidol, epichlorohydrin, or mixtures of at least two of them. The epoxide is often epichlorohydrin.

The basic agent may be chosen from alkali or alkaline-earth metal oxides, hydroxides, carbonates, hydrogen carbonates, phosphates, hydrogen phosphates and borates, and mixtures thereof. Alkali and alkaline-earth metal oxides and hydroxides are preferred.

In one particular embodiment the chlorohydrin is dichloropropanol, the basic agent is an alkali and/or alkaline-earth metal hydroxide and the epoxide is epichlorohydrin.

In the process for manufacturing the epoxide according to the invention, the dehydrochlorination reaction may be carried out such as described in WO 2005/054167 in the name of SOLVAY SA, the content of which is hereby incorporated by reference, more specifically the passage from page 19, line 12 to page 22, line 30.

In the process for manufacturing the epoxide according to the invention, the dehydrochlorination reaction may be carried out such as described in WO 2006/100311 in the name of SOLVAY SA, the content of which is hereby incorporated by reference, more specifically the passages at page 2, lines 22 to 25, and from page 22, line 28 to page 23, line 35.

In the process for manufacturing the epoxide according to the invention, the dehydrochlorination reaction may be carried out such as described in WO 2008/101866 in the name of SOLVAY SA, the content of which is hereby incorporated by reference, more specifically the passage from page 2, line 1 to page 13, line 16.

In the process for manufacturing the epoxide according to the invention, the dehydrochlorination reaction may be carried out such as described in WO 2008/152045 in the name of SOLVAY SA, the content of which is hereby incorporated by reference, more specifically the passages from page 9, line 22, to page 13, line 31.

In the process for manufacturing the epoxide according to the invention, the dehydrochlorination reaction may be carried out such as described in WO 2008/152043 in the name of SOLVAY SA, the content of which is hereby incorporated by reference, more specifically the passages from page 7, line 35, to page 8, line 25.

The process for manufacturing the epoxide according to the invention may be integrated in a global scheme for preparing dichloropropanol such as described in WO 2006/106155 in the name of SOLVAY SA, the content of which is hereby incorporated by reference, more specifically the passages at page 2, lines 26 to 31, and from page 22, line 10 to page 23, line 19.

In the process for manufacturing the epoxide according to the invention, the dehydrochlorination reaction may be carried out such as described in WO 2006/100318 in the name of SOLVAY SA, the content of which is hereby incorporated by reference, more specifically the passages at page 2, lines 23 to page 3, line 26, and from page 24, line 17 to page 31, line 18.

The process for manufacturing the epoxide according to the invention may also comprise a step of treating water effluents such as described in WO 2009/095429 in the name of SOLVAY SA, the content of which is hereby incorporated by reference, more specifically the passages from page 1, line 24, to page 27, line 26.

The invention also relates to a process for manufacturing an epoxy derivative selected from the group consisting of epoxy resins, glycidyl ethers, glycidyl esters, glycidyl amides, glycidyl imides, glycidyl amines, products that can be used as coagulants, wet-strength resins, cationization agents, flame retardants, ingredients for detergents, epichlorohydrin elastomers, halogenated polyethers-polyols, monochloropropanediol, and any mixture of at least two of them, comprising the process for manufacturing the epoxide in which the epoxide is epichlorohydrin, and in which the epichlorohydrin is subjected to a reaction with at least one compound chosen from monoalcohols, monocarboxylic acids, polyols, polyamines, amino alcohols, polyimides, polyamides, polycarboxylic acids, ammonia, amines, polyaminoamides, polyimines, amine salts, phosphoric acid, phosphoric acid salts, phosphorus oxychlorides, phosphoric acid esters, phosphonic acids, esters of phosphonic acids, salts of phosphonic acids, phosphinic acids, esters of phosphinic acids, salts of phosphinic acids, phosphine oxides, phosphines, ethoxylated alcohols, alkylene or phenylene oxides, and mixtures of at least two of them, or in which the epichlorohydrin according to the invention is subjected to a homopolymerization reaction, or in which epichlorohydrin is subjected to a reaction of oligomerisation, of co-oligomerisation, of condensation, of dehydrochlorination and of hydrolysis, with water, or with a di- or polyhydroxylated compound which may optionally be halogenated and/or have ether oxide bonds and/or double bonds capable of being halogenated in a subsequent stage, or wherein epichlorohydrin is subjected to a reaction with water.

The process for manufacturing the epoxy derivative according to the invention, may be carried out, such as described in Application WO 2008/152045 in the name of SOLVAY SA, the content of which is hereby incorporated by reference, more specifically the passages from page 32, line 6, to page 63, line 4, and in Application WO 2008/152044 in the name of SOLVAY SA, the content of which is hereby incorporated by reference, more specifically the passages from page 13, line 22, to page 44, line 8 and in Application PCT/EP2009/053766, in the name of SOLVAY SA, the content of which is hereby incorporated by reference, more specifically the passages from page 27, line 10, to page 33, line 7.

BRIEF DESCRIPTION OF THE DRAWINGS

FIG. 1 is a purification process and the equipment according to the invention.

The purification process and the equipment according to the invention will now be illustrated with reference to FIG. 1. This FIGURE schematically represents a practical embodiment of aspects of the invention. The hydrogen chloride gas originates from an isocyanate manufacturing unit and is contaminated with impurities essentially composed of monochlorobenzene in an amount of 250 ppm.

According to a first embodiment, the scrubbing agent is essentially composed of dichloropropanol that originates from a plant for manufacturing dichloropropanol by hydrochlorination of glycerol using hydrogen chloride. The purified hydrogen chloride is conveyed to a glycerol hydrochlorination unit.

A first gas stream containing the hydrogen chloride to be purified is introduced via the line (4) into section (2) of the scrubbing column (1). A first liquid stream essentially composed of fresh dichloropropanol (necessary for boosting the supply, considering the entrainment by vapour pressure of the dichloropropanol to the glycerol hydrochlorination unit via the purified hydrogen chloride and the removal of dichloropropanol via the purge system (see below)) is introduced via the line (5) into section (3) of the scrubbing column (1). Section (2) of the scrubbing column (1) is preferably packed with Berl saddles. Section (3) of the scrubbing column (1) is preferably packed with bubble trays. A second liquid stream comprising the dichloropropanol, in which the impurities extracted from the hydrogen chloride to be purified are dissolved, and a portion of this hydrogen chloride is withdrawn at the bottom of the column (1) via the line (6) and recycled in a loop to the top of section (2) via the pump (7) and the line (8). A portion of this second liquid stream, which constitutes a third liquid stream, is drawn off via the line (9) and supplies a stripping column (10). A second gas stream comprising most of the hydrogen chloride dissolved in the third liquid stream is drawn off from the stripping column (10) and sent back to section (2) of the scrubbing column (1) via the line (12). A fourth liquid stream comprising the dichloropropanol enriched with impurities from the hydrogen chloride is drawn off from the column (10) and sent to a distillation column (16) via the line (11). A fifth liquid stream enriched with impurities from the hydrogen chloride, the boiling point of which is below that of dichloropropanol, is drawn off from the column (16) via the line (14). This fifth stream may be sent to a storage unit or to a high-temperature oxidation unit. A sixth liquid stream enriched with dichloropropanol is drawn off from column (16) and sent to section (2) of the scrubbing column (1) via the line (17). A seventh liquid stream enriched with impurities from the hydrogen chloride, the boiling point of which is above that of dichloropropanol, is drawn off from the column (16) via the line (15). This seventh stream may be sent to a storage unit or to a high-temperature oxidation unit.

A third gas stream comprising the purified hydrogen chloride gas exits the column (1) via the line (13) in order to be conveyed to the glycerol hydrochlorination unit.

By virtue of this equipment, the monochlorobenzene content of the HCl may be reduced from 250 ppm to less than 10 ppm in the third gas stream exiting the column (1) via the line (13). This operation therefore makes it possible to effectively purify the hydrogen chloride of monochlorobenzene. In this way a product is obtained that can be used, without drawbacks, for a glycerol hydrochlorination step.

According to a second embodiment, the scrubbing agent is essentially composed of a purge stream that orginates from a plant for manufacturing dichloropropanol by hydrochlorination of glycerol using hydrogen chloride. The purified hydrogen chloride is conveyed to a glycerol hydrochlorination unit.

In a first variant of the second embodiment, the procedure of the first embodiment is followed, except that the purge stream is used instead of the dichloropropanol in the various lines and columns.

In a second variant of the second embodiment, the procedure of the first variant is followed, except that line (17) does not exist.

In a third variant of the second embodiment, the procedure of the first variant is followed, except that the distillation column (16) and the lines (14), (15) and (17) do not exist, and the stream drawn off via the line (11) supplies a high-temperature oxidation unit.

In a fourth variant of the second embodiment, the procedure of the second variant is followed, except that the stripping column (10) and the lines (11) and (12) do not exist, and the stream drawn off via the line (9) supplies a high-temperature oxidation unit.

EXAMPLE 1 (ACCORDING TO THE INVENTION)

Hydrogen chloride has been introduced at a constant flow rate through a gas dispersion tube made of fritted glass in liquid 1,3-dichloropropan-2-ol contained in a glass flask maintained at 25° C., and at a pressure of 1 bar. The hydrogen chloride contained initially chlorobenzene at a concentration of 1000 ppm by weight. The flow rate of the hydrogen chloride has been set in order to treat 1.6 g of gas with 1 g of 1,3-dichloropropan-2-ol in 2 h. The residence time was about 5 s. The hydrogen chloride at the output of the treatment has been sampled and analyzed several times during the treatment and at the end of the treatment. The content in chlorobenzene of the gas was always lower than 300 ppm by weight.

EXAMPLE 2 (ACCORDING TO THE INVENTION)

The conditions of example 1 have been used except that the flow rate of the hydrogen chloride has been set in order to treat 2.6 g of gas with 1 g of 1,3-dichloropropan-2-ol in 2 h. The residence time was about 2.5 s. The hydrogen chloride at the output of the treatment has been sampled and analyzed several times during the treatment and at the end of the treatment. The content in chlorobenzene of the gas was always lower than 300 ppm by weight.

EXAMPLE 3 (ACCORDING TO THE INVENTION)

The conditions of example 1 have been used except that the flow rate of the hydrogen chloride has been set in order to treat 6.5 g of gas with 1 g of 1,3-dichloropropan-2-ol in 4 h. The residence time was about 2.5 s. The hydrogen chloride at the output of the treatment has been sampled and analyzed several times during the treatment and at the end of the treatment. The content in chlorobenzene of the gas was always lower than 500 ppm by weight.

The invention claimed is:

1. A process, comprising bringing hydrogen chloride into contact with a scrubbing agent comprising a chlorohydrin to produce purified hydrogen chloride, and reacting a polyhydroxylated aliphatic hydrocarbon, an ester of a polyhydroxylated aliphatic hydrocarbon, or a mixture of the two with a chlorinating agent comprising said purified hydrogen chloride in order to obtain a chlorohydrin.

2. The process according to claim 1, wherein at least one portion of the hydrogen chloride to be purified is in the gaseous state.

3. The process according to claim 1, wherein the hydrogen chloride to be purified comprises an aromatic organic compound.

4. The process according to claim 1, wherein the hydrogen chloride to be purified is the by-product of the manufacture of an organic isocyanate.

5. The process according to claim 4, wherein the hydrogen chloride to be purified is the by-product of the manufacture of an organic isocyanate by reacting phosgene with an organic amine.

6. The process according to claim 3, wherein the aromatic organic compound is a chloroaromatic compound.

7. The process according to claim 1, wherein the chlorohydrin in the scrubbing agent is selected from the group consisting of monochloropropanediol, dichloropropanol, and mixtures thereof.

8. The process according to claim 1, wherein the scrubbing agent further comprises at least one compound selected from the group consisting of water, alcohols, aldehydes, ketones, carboxylic acids, carboxylic acid esters, ethers, halogenated hydrocarbons, epoxides, metals, and mixtures of at least two of them.

9. The process according to claim 1, wherein the scrubbing agent is substantially composed of dichloropropanol in the liquid state.

10. The process according to claim, wherein bringing hydrogen chloride into contact with the scrubbing agent is carried out at a temperature between 10 and 120° C., and at a pressure between 1 and 20 bar absolute.

11. The process according to claim 1, wherein a flow of the scrubbing agent is between 0.5 and 50% by weight relative to a flow of hydrogen chloride to be purified.

12. A process as claimed in claim 1, further comprising subjecting said chlorohydrin produced by reacting a polyhydroxylated aliphatic hydrocarbon, an ester of a polyhydroxylated aliphatic hydrocarbon, or a mixture of the two with a chlorinating agent to a dehydrochlorination reaction to provide an epoxide.

13. A process for manufacturing an epoxy derivative selected from the group consisting of epoxy resins, glycidyl ethers, glycidyl esters, glycidyl amides, glycidyl imides, glycidyl amines, products that can be used as coagulants, wet-strength resins, cationization agents, flame retardants, ingredients for detergents, epichlorohydrin elastomers, halogenated polyethers-polyols, monochloropropanediol, and any mixture of at least two of them, comprising:

CARRYING out the process according to claim 12, wherein the epoxide is epichlorohydrin, and subjecting the epichlorohydrin to a reaction with at least one compound selected from the group consisting of monoalcohols, monocarboxylic acids, polyols, polyamines, amino alcohols, polyimides, polyamides, polycarboxylic acids, ammonia, amines, polyaminoamides, polyimines, amine salts, phosphoric acid, phosphoric acid salts, phosphorus oxychlorides, phosphoric acid esters, phosphonic acids, esters of phosphonic acids, salts of phosphonic acids, phosphinic acids, esters of phosphinic acids, salts of phosphinic acids, phosphine oxides, phosphines, ethoxylated alcohols, alkylene or phenylene oxides, and mixtures of at least two of them, or to a homopolymerization reaction, or to a reaction of oligomerisation, of co-oligomerisation, of condensation, of dehydrochlorination and of hydrolysis, with water, or with a di- or polyhydroxylated compound which may optionally be halogenated and/or have ether oxide bonds and/or double bonds capable of being halogenated in a subsequent stage, or to a reaction with water.

14. The process according to claim 1, comprising reacting said polyhydroxylated aliphatic hydrocarbon, said ester of a polyhydroxylated aliphatic hydrocarbon, or said mixture of the two with said chlorinating agent comprising said purified hydrogen chloride in order to obtain dichloropropanol.

15. The process according to claim 14, wherein said scrubbing agent comprises dichloropropanol.

* * * * *